United States Patent
Li et al.

(10) Patent No.: US 11,268,071 B2
(45) Date of Patent: Mar. 8, 2022

(54) ADDITION OF NUCLEASES DIRECTLY TO CELL CULTURE TO FACILITATE DIGESTION AND CLEARANCE OF HOST CELL NUCLEIC ACIDS

(71) Applicant: Merck Sharp & Dohme Corp., Rahway, NJ (US)

(72) Inventors: Yi Li, Westford, MA (US); Matthew Woodling, Lansdale, PA (US); Adam Kristopeit, Lansdale, PA (US)

(73) Assignee: Merck Sharp and Dohme Corp., Rahway, NJ (US)

( * ) Notice: Subject to any disclaimer, the term of this patent is extended or adjusted under 35 U.S.C. 154(b) by 0 days.

(21) Appl. No.: 16/498,013

(22) PCT Filed: Mar. 28, 2018

(86) PCT No.: PCT/US2018/024739
§ 371 (c)(1),
(2) Date: Sep. 26, 2019

(87) PCT Pub. No.: WO2018/183429
PCT Pub. Date: Oct. 4, 2018

(65) Prior Publication Data
US 2020/0040310 A1    Feb. 6, 2020

Related U.S. Application Data

(60) Provisional application No. 62/478,895, filed on Mar. 30, 2017.

(51) Int. Cl.
| | |
|---|---|
| A61K 38/17 | (2006.01) |
| A61K 39/00 | (2006.01) |
| C12N 5/078 | (2010.01) |
| A61K 31/7088 | (2006.01) |
| A61K 35/18 | (2015.01) |
| C12N 7/00 | (2006.01) |
| C12N 5/071 | (2010.01) |
| C12N 9/22 | (2006.01) |
| C07K 4/04 | (2006.01) |
| C12N 5/07 | (2010.01) |
| C12N 15/10 | (2006.01) |

(52) U.S. Cl.
CPC ............... *C12N 7/00* (2013.01); *C07K 4/04* (2013.01); *C12N 5/06* (2013.01); *C12N 5/0686* (2013.01); *C12N 9/22* (2013.01); *C12N 15/101* (2013.01); *C12N 15/1017* (2013.01); *A61K 2039/5254* (2013.01); *C12N 2501/70* (2013.01); *C12N 2501/73* (2013.01); *C12N 2531/00* (2013.01); *C12N 2533/12* (2013.01); *C12N 2533/54* (2013.01); *C12N 2533/78* (2013.01); *C12N 2700/00* (2013.01); *C12N 2770/24121* (2013.01); *C12N 2770/24134* (2013.01); *C12N 2770/24151* (2013.01)

(58) Field of Classification Search
CPC .............. A61K 2300/00; A61K 38/177; A61K 38/1774; A61K 39/00; A61P 27/16
See application file for complete search history.

(56) References Cited

U.S. PATENT DOCUMENTS

| | | | |
|---|---|---|---|
| 2004/0137013 A1* | 7/2004 | Katinger | C12N 7/00 424/199.1 |
| 2010/0285059 A1 | 11/2010 | Shenk et al. | |
| 2012/0219588 A1 | 8/2012 | Thompson et al. | |
| 2016/0199478 A1* | 7/2016 | Kistner | C07K 16/1081 424/159.1 |
| 2020/0392468 A1 | 12/2020 | Li et al. | |

FOREIGN PATENT DOCUMENTS

| | | |
|---|---|---|
| EP | 0870508 A1 | 10/1998 |
| EP | 1358319 B1 | 6/2009 |
| WO | 2007021672 A2 | 2/2007 |

OTHER PUBLICATIONS

Caballero et al., Evaluation of the Serratia marcescens nuclease (NucA) as a transgenic cell ablation system in porcine, Animal Biotechnology, 2009, 177-185, 20-4.
Langfield et al., Manufacture of measles viruses, Methods in Molecular Biology, 2011, 345-366, 737.
Lee et al., Combined in-fermenter extraction and cross-flow microfiltration for improved inclusion body processing, Biotechnology Bioeng., 2004, 103-113, 85-1.
Li et al., Removing residual DNA from Vero-cell culture-derived human rabies vaccine by using nuclease, Biologicals, 2014, 271-276, 5.
Puig et al., Canine adenovirus downstream processing protocol, Methods in Molecular Biology, 2014, 197-210, 1089.

* cited by examiner

*Primary Examiner* — Barry A Chestnut
(74) *Attorney, Agent, or Firm* — Matthew A. Leff; Alysia A. Finnegan

(57) ABSTRACT

The present invention provides an efficient process for culturing viruses in the presence of an endonuclease and for producing vaccines, typically from live attenuated viruses, under conditions to reduce the presence of host cell DNA and eliminate the need for a post-harvest DNA digestion step.

20 Claims, 23 Drawing Sheets

Virus Mass by Western HCMV Glycoprotein Mass Assay

FIG.11A

ADDITION OF NUCLEASES DIRECTLY TO CELL CULTURE TO FACILITATE DIGESTION AND CLEARANCE OF HOST CELL NUCLEIC ACIDS

FIELD OF THE INVENTION

The present invention is in the field of virology and vaccine development and relates to an improved method of manufacture of a viral vaccine, particularly of a whole-virus vaccine, preferably of an attenuated live vaccine.

BACKGROUND OF THE INVENTION

The use of cell culture technology for the production of vaccines is critical for the large scale production of many vaccines based on replication-competent viruses (e.g., live attenuated viruses and inactivated viruses) in use today. Many attempts have therefore been undertaken in the art to utilize standard tissue culture technology with established mammalian cell lines, such as MDCK (Madin-Darby Canine Kidney) or Vero (African Green Monkey Kidney) cells, for virus production.

With the use of cell culture, a particular concern for regulatory agencies is the presence of contaminants such as host cell DNA (HcDNA). The criteria for safety, efficacy, and potency of vaccines for testing and/or use in humans is governed by Title 21 of the U.S. Code of Federal Regulations. Current Good Manufacturing Practices (cGMP) guidelines include specifications for acceptable levels of residual HcDNA which are defined to be <10 ng/dose with a median size of <200 bp. See, e.g., FDA Briefing Document, Vaccines and Related Biological Products, Advisory Committee Meeting, Sep. 19, 2012. While defined specifications are not provided for host cell RNA (HcRNA), it is desirable to manufacture a drug substance where this residual is as low as practically attainable. The reduction or removal of HcDNA/HcRNA during downstream processing is often facilitated by a dedicated enzymatic nucleic acid digestion step and/or purification steps (e.g., chromatography) to decrease the amount of nucleic acids and/or their size.

In a typical exemplification, a live virus vaccine or viral vector is produced by infection of mammalian host cells grown in a bioreactor vessel. Following cell separation, filtered culture medium containing the crude vaccine product is incubated with an endonuclease, such as Benzonase® for a defined period of time to allow digestion of HcDNA/HcRNA after which the nucleic acid fragments are removed by one of various unit operations including diafiltration, chromatography, centrifugation, etc. See, e.g., Li et al., 2014, Biologicals 42(5):271-6; Puig et al., 2014, Methods Mol Biol. 1089:197-210; Langfield et al., 2011, Methods Mol Biol. 737:345-66; and Caballero et al., 2009, Anim Biotechnol. 20(4):177-85; Lee et al., 2004, Biotechnol Bioeng. 85(1):103-13; and U.S. Pat. No. 9,012,198.

European Patent Application Publication EP 0870508A1 discloses a method to produce a viral antigen vaccine by infecting an animal cell line with virus, propagating virus in the cell culture in a fermenter, adding a nuclease to the cell culture shortly before the end of virus propagation to digest nucleic acid material released from the lysing host cells into the medium, harvesting the virus and obtaining viral antigens thereof by extraction in order to make the viral antigen vaccine.

European Patent No. EP 1358319B1 discloses a method to produce a live attenuated influenza vaccine in a single step procedure involving additional of an endonuclease, such as Benzonase®, and a protease to the virus-infected cell suspension culture in Roux bottles or roller bottles that does not require any chromatographic or other purification steps of the virus suspension harvested from the cell culture supernatant by centrifugation, particularly no protein separation or purification steps.

SUMMARY OF THE INVENTION

The present invention relates to the addition of an endonuclease (e.g., Benzonase®) to an infected cell culture to realize efficient HcDNA removal. In one embodiment, the present invention relates to a method for making a vaccine, comprising the steps of: a) culturing ARPE-19 cells or Vero cells, as adherent cells on static surfaces or on microcarriers, b) infecting the ARPE-19 cells with cytomegalovirus or the Vero cells with a flavivirus (e.g., a Dengue virus); and c) treating the infected cell supernatant with Benzonase® and its co-factor, magnesium, during the virus production phase (post- or at infection prior to supernatant harvest), as to digest free HcDNA from lysed cells. In one aspect of this embodiment, the cells are ARPE-19 cells cultured on microcarriers. In another aspect of this embodiment, the cells are Vero cells cultured on microcarriers or on a static plastic surface such as a tissue culture flask.

BRIEF DESCRIPTION OF THE DRAWINGS

FIG. 5B is a zoomed in view of FIG. 5A.

FIGS. 11A-B are plots of HCMV viral mass (A: as measured by Western HCMV glycoprotein assay) and viral infectivity (B: as measured by cell based infectivity assay) under various reactor conditions post harvest and post clarification, and in the case of the control arms, 2 hr post Benzonase® incubation after clarification.

DETAILED DESCRIPTION OF THE INVENTION

Figure 1:
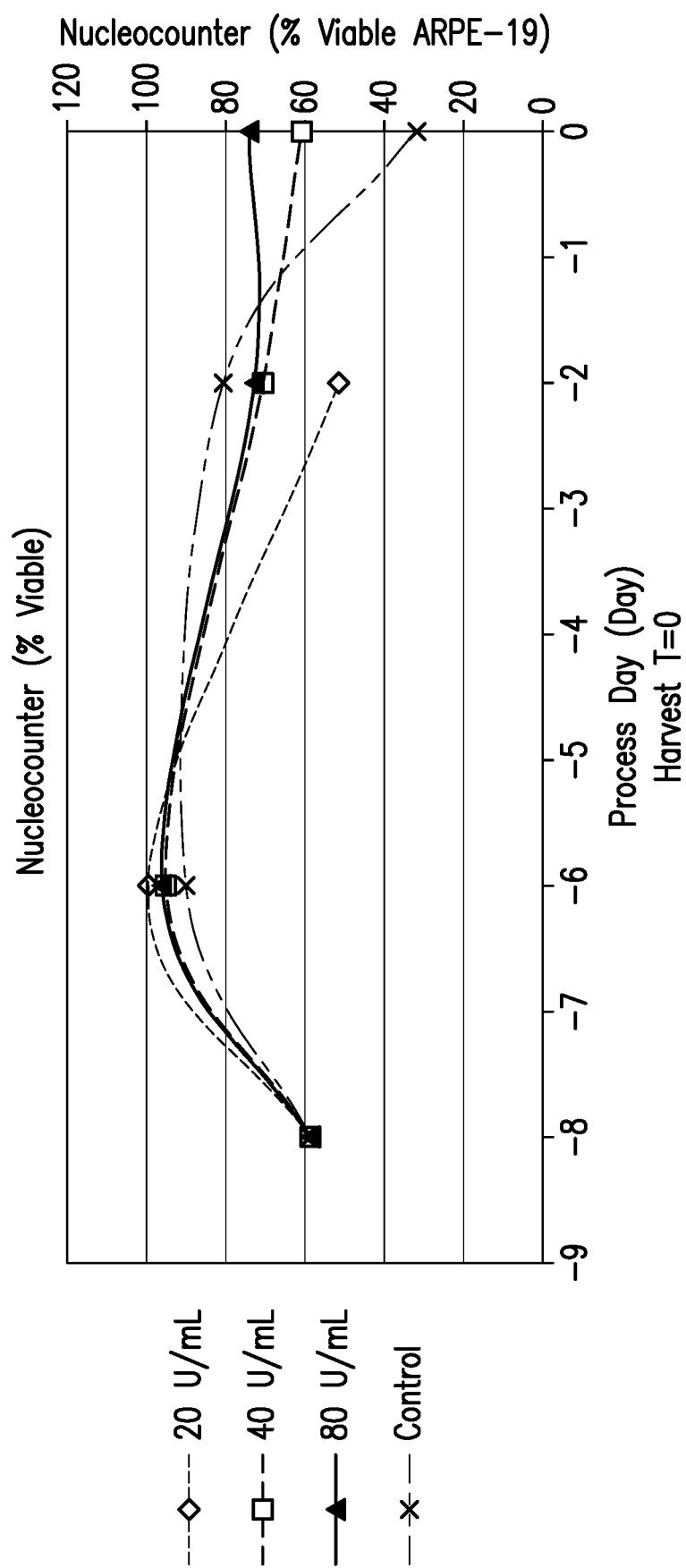
FIG. 1 is a plot of ARPE-19 cell viability on microcarriers (as measured by a NucleoCounter® cell counter) over time before supernatant harvest with different concentrations of Benzonase®.
Figure 2A:
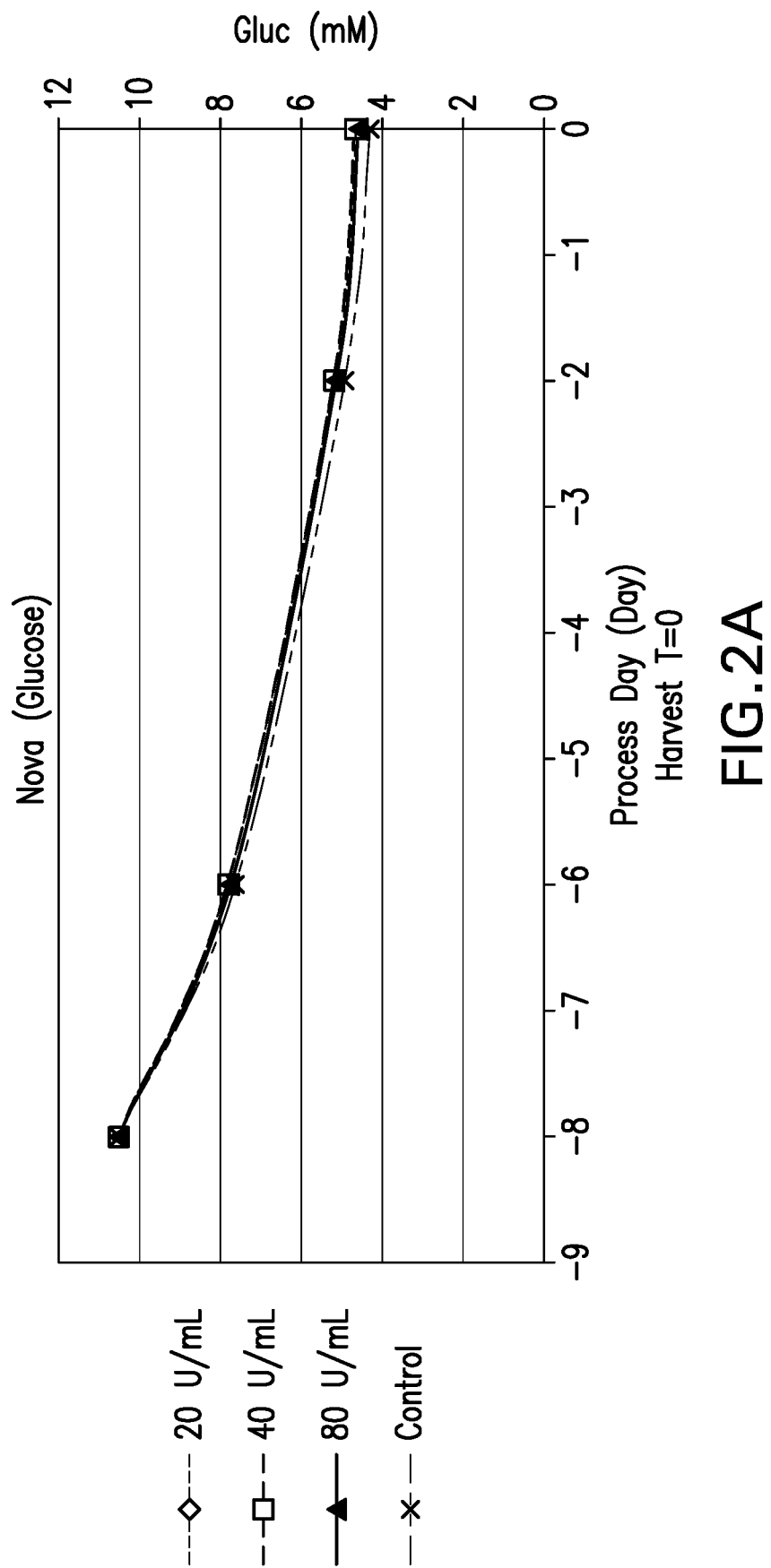
FIGS. 2A-D are plots of various indicators of ARPE-19 cell metabolism grown adherently on microcarriers in the presence of Benzonase® (A: glucose; B: lactate; C: glutamine; D: pH) as measured by a BioProfile® Flex over time before supernatant harvest.
Figure 2B:
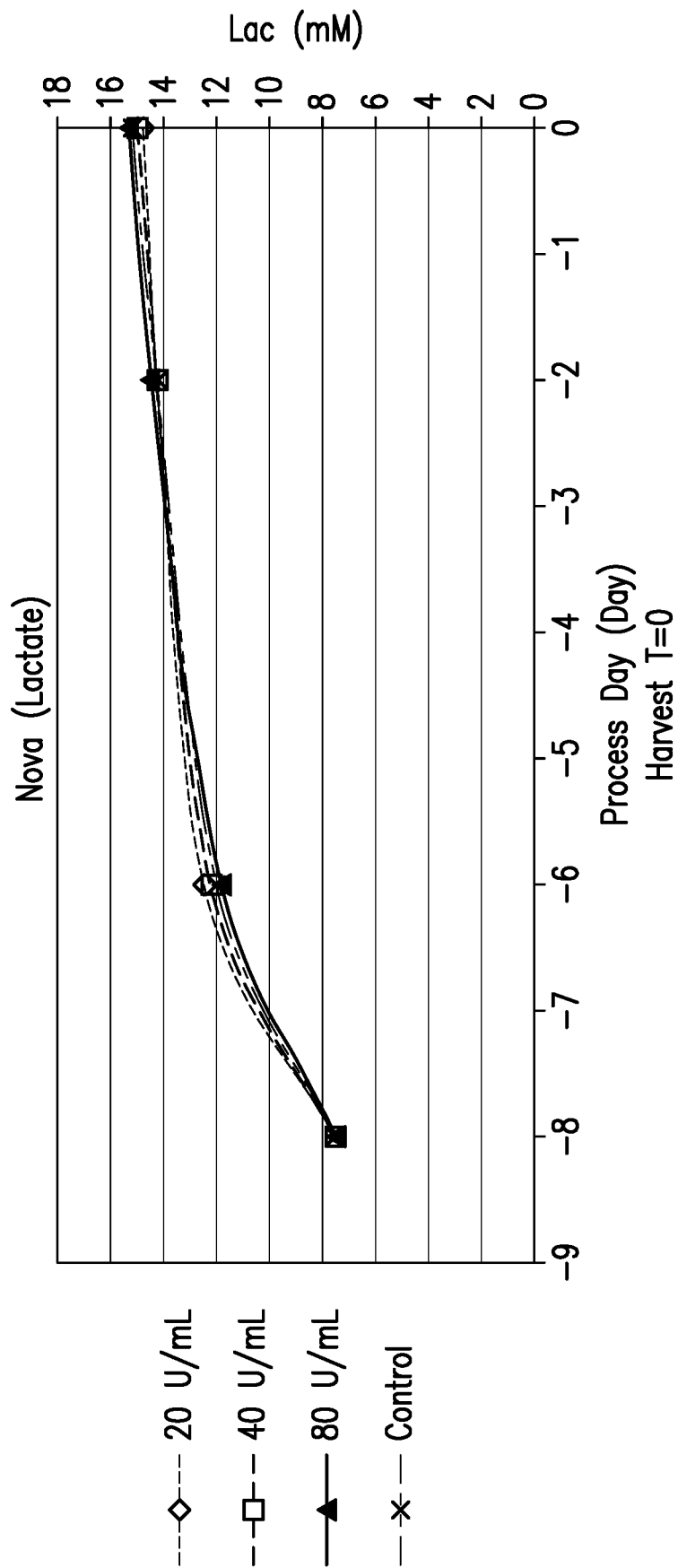
Figure 2C:
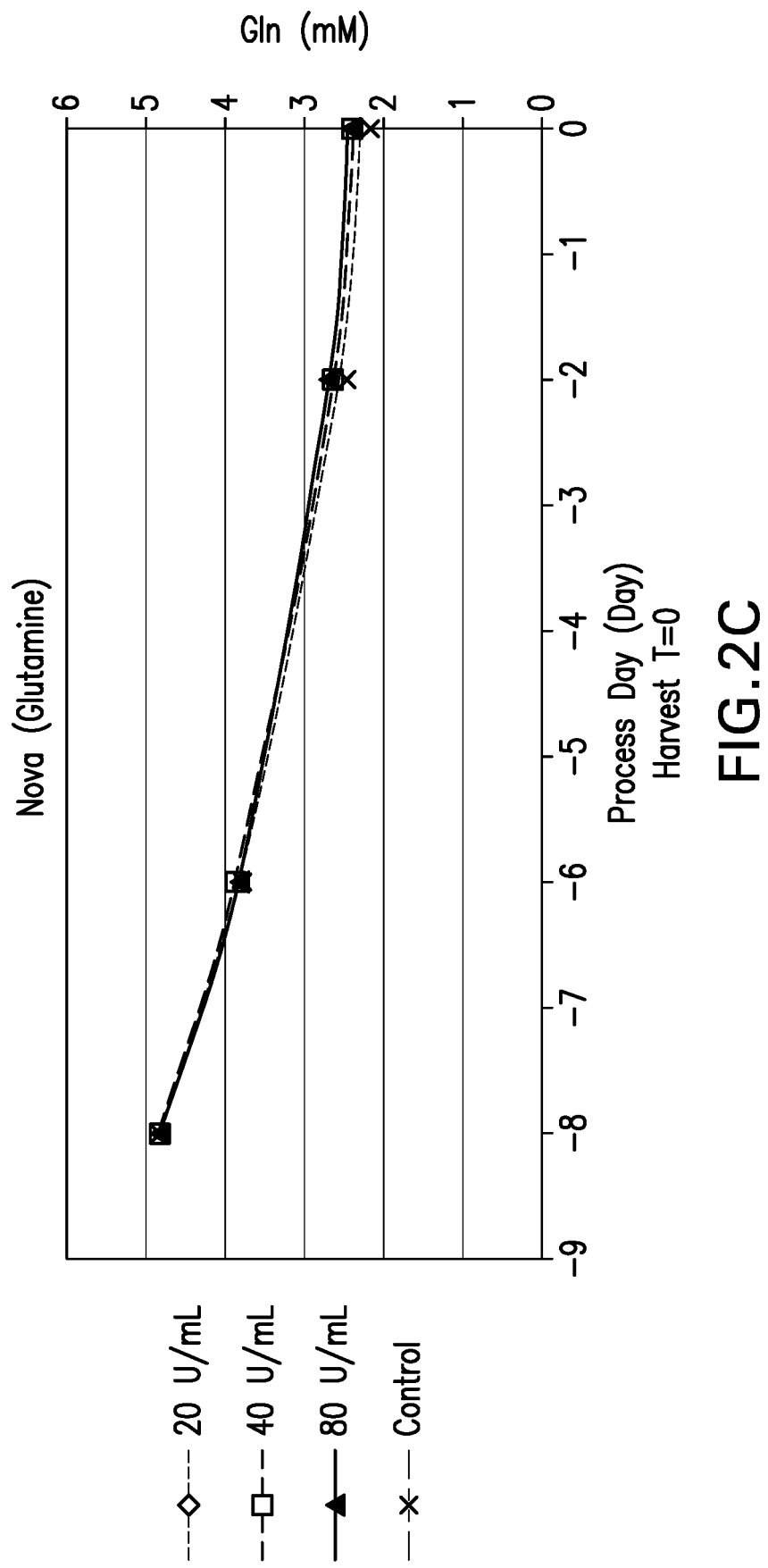
Figure 2D:
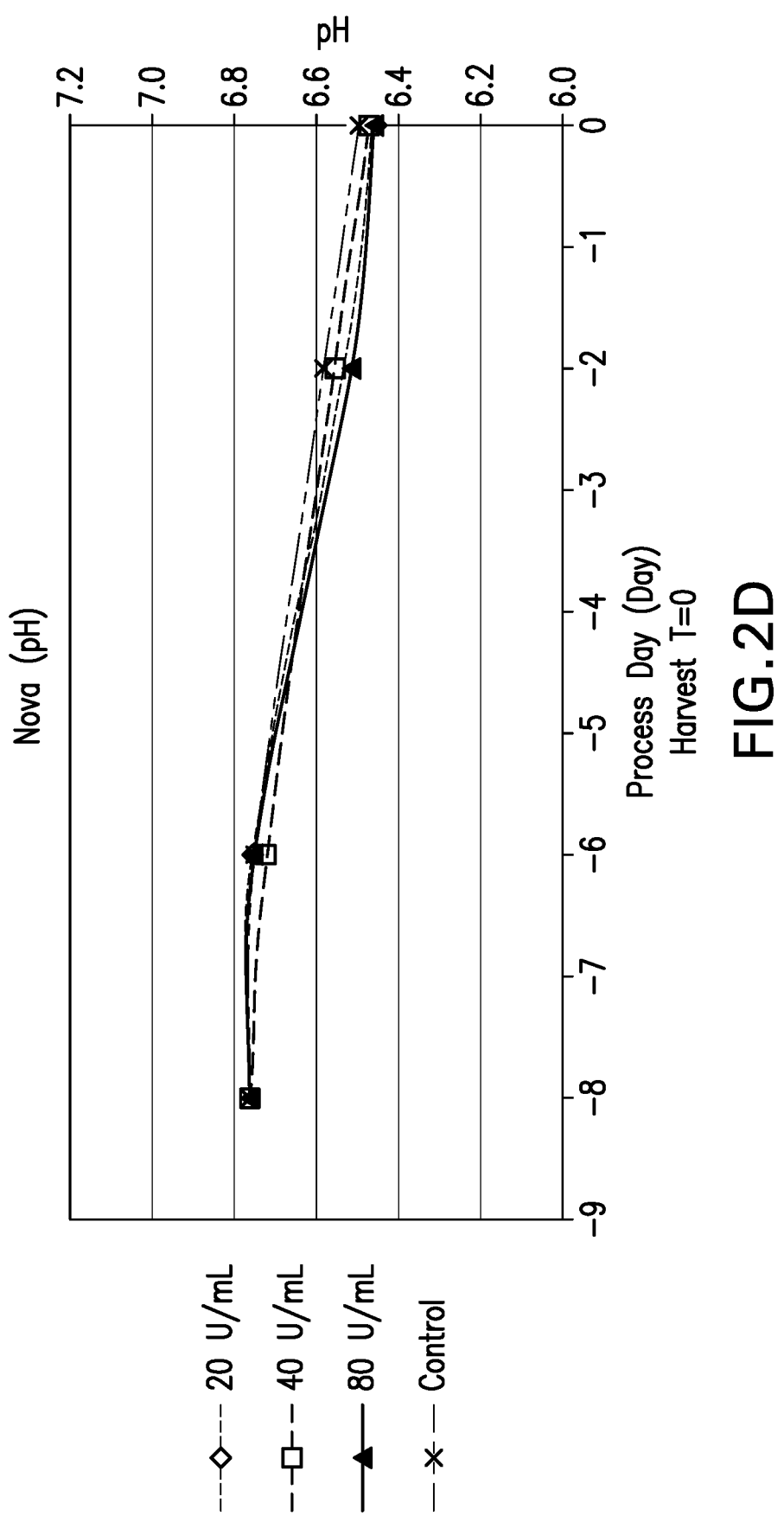

The present invention relates to the addition of a nuclease, such as Benzonase®, directly to a bioreactor or cell culture flask in which cell culture and viral vaccine production occur. The present invention is based on simplification of the bioprocess for vaccine manufacturing. In particular, the present invention is based on the addition of a single dose of highly active endonuclease. This is exemplified for a genetically attenuated human cytomegalovirus (HCMV) produced from infected human retinal pigment epithelial cells (ARPE-19) grown adherently on microcarriers and a live attenuated Dengue vaccine produced from infected monkey kidney epithelial cells (Vero) grown as adherent cells on static cell culture surfaces such as flasks or grown adherently on microcarriers, and is expected to be broadly applicable to other mammalian cell substrates used to produce viral vaccines.

As shown in the Examples, the addition of nuclease directly to cell culture was demonstrated to be non-detrimental to ARPE19 or Vero cell culture as well as human cytomegalovirus (HCMV) or Dengue virus production in their respective cell lines. Moreover, the addition of nuclease was specifically demonstrated for a HCMV virus infected ARPE-19 cell culture in a bioreactor platform with microcarriers. In particular, it was unexpected that this approach would work with cells grown adherently on microcarriers. Growing cells on microcarriers, compared to adherent cells or suspensions in roller bottles, requires greater agitation to suspend the microcarriers and subjects the cells to greater shear stress. See, e.g., Croughan et al., 1987, Biotechnol Bioeng.29:130-41. The increased shear stress may affect the permeability of the cells exposing them to the nuclease thereby decreasing cell viability.

Several potential advantages exist relative to addition of a nuclease post-harvest: (1) purification processing time is reduced by elimination of a separate nucleic acid digestion step which generally increases viral potency yield; (2) the efficiency of nucleic acid digestion is increased since digestion in the bioreactor occurs for 0.5-8.0 days under cell culture conditions (during virus production) as opposed to a separate stand-alone unit operation carried out in a holding tank typically for 1-12 hr at room temperature or at 2-8° C. (the use of a holding tank can be detrimental to viruses that are unstable resulting in degradation in quality over a period of hours); (3) elimination of a separate unit operation including capital equipment such as a dedicated holding tank lowers manufacturing costs; (4) increased digestion efficiency reduces the total amount of enzyme required and can lower manufacturing costs; and (5) increased digestion efficiency towards minimal residual HcDNA as HcDNA will be accessible to Benzonase® digestion as soon as it is released from lysed cells into the Benzonase® containing cell media. Such immediate digestion will decrease the potential for HcDNA-HCP aggregates that could cause a burden on the purification process.

The Examples provided herein demonstrate that a single addition of an endonuclease, such as Benzonase®, is effective for several days and that enzyme amounts may be titrated to control rate and extent of nucleic acid digestion. The early addition of nuclease (e.g., Benzonase®) to the virus-infected ARPE19 or Vero-cell culture had no negative implications on the virus yield and cell health. Furthermore, viral stability was observed over longer incubation times with the endonuclease (up to 8 days for HCMV or up to 15 days for Dengue).

Accordingly, the present invention is directed to a method for production of a virus, comprising the steps of: a) infecting a culture of cells in a cell culture medium with a desired virus; and b) incubating the cells in cell culture medium containing endonuclease for up to 8 days for HCMV and up to 15 days for Dengue, wherein the endonuclease is added to the cell culture medium at any time from initial infection of the cells to prior to harvesting the cells. In one embodiment, the cells are grown adherently on microcarriers. In another embodiment, the cells are adhered to a static plastic surface. Examples of static plastic surfaces include, but are not limited to, cell stacks, cell factory systems, T-flasks, HYPERFlasks™, HYPERStacks™, and the like.

In certain embodiments, the endonuclease is added at the time of initial infection. In certain embodiments, the endonuclease is added from 0.5 to 8 days prior to harvesting the cells for HCMV or from 0.5 to 15 days prior to harvesting the cells for Dengue. Included herein is adding the endonuclease from 0.5, 1, 2, 3, 4, 5, 6, 7, 8, days prior to harvesting the cells for HCMV or Dengue, and additional from 9, 10, 11, 12, 13, 14, or 15 days prior to harvesting the Dengue cells. In certain embodiments, the endonuclease can be added multiple times during the virus production phase. For example, the endonuclease can be added 2, 3, 4, 5, 6, 7, 8, 9 or 10 times during the virus production phase. Where the endonuclease is added multiple times, the total amount of endonuclease added can be equivalent to the amounts used for a single addition as described herein or the total amount of endonuclease can be a multiple of the amount for a single addition (e.g., 2×, 3×, 4×, 5×, 6×, 7×, 8×, 9×, or 10× the amount of a single addition as described herein). In certain embodiments, the endonuclease can be continuously added, for example, through perfusion, using overall amounts of endonuclease as described herein.

In the methods of the present invention, the cells used for cell culture and viral propagation may be primary cells or any cultured cell line suitable for producing the virus. In certain embodiments, the cells are obtained from a continuous cell line. Examples of cells which may be used include mammalian cells (e.g., ARPE-19, CHO, BHK, African green monkey kidney derived Vero, Madin-Darby Canine Kidney cells (MDCK), PBS-1 cells, HeLa cells, RK, RK44, RK13, MRC-5, CEF, diploid monolayer cells or PER.C6® cells), avian cells (e.g, chicken embryo fibroblasts, or continuous cell lines from an avian) and insect cells (e.g, Sf9 cells). The cells may be grown adherently on static plastic surfaces, such as in roller bottles, flasks, cell factories, or may be grown adherently on microcarriers, or in suspension cultures in stirred-tank bioreactors or disposable wave bioreactors. The microcarriers may be made of any suitable surface for cell culture, including, but not limited to, dextran, collagen, polystyrene, polyacrylamide, gelatine, glass, cellulose, polyethylene and plastic. In certain embodiments, the cells are grown adherently on microcarriers. In embodiments where microcarriers are used, it is preferable not to include trypsin during the virus production phase because the presence of trypsin would remove cells from the microcarriers. In one particular embodiment, the microcarriers are Cytodex® 1 microcarriers, dextran-based spheres with diethylaminoethyl functionality, available from GE Healthcare Life Sciences.

In particular preferred embodiments, the cells are in form of a cell culture. Cell culture media used in the methods of the invention can be selected from standard media, sometimes with serum/other supplements, or with media specifically developed for the application. In certain embodiments of the invention, the cell culture media contains serum. In certain embodiments when HCMV or Dengue is propagated, the cell culture medium in which the infected cells are grown contains no, or very minimal, amounts of trypsin. In additional embodiments when HCMV or Dengue is propagated, trypsin is not added to the cell culture medium in which the infected cells are grown.

In the methods of the present invention, the viruses are selected from enveloped DNA or RNA viruses, with single or double (DNA) stranded genomes, sense or antisense, continuous or segmented. In preferred embodiments of the invention, the viruses are selected from the group of enveloped viruses, including, flaviviruses, togaviruses, retroviruses, coronaviruses, filoviruses, rhabdoviruses, bunyaviruses, orthomyxoviruses, paramyxoviruses, arenaviruses, hepadnaviruses, herpesviruses, and poxviruses. In other preferred embodiments, the viruses are flaviruses, coronaviruses, orthomyxoviruses, herpesviruses or togaviruses. In one particularly preferred embodiment, the virus is selected from the herpesviruses, for example, a cytomegalovirus strain or a flavivirus, for example, a Dengue virus.

In some embodiments, the cytomegalovirus is a genetically attenuated human cytomegalovirus as described in U.S. Pat. No. 9,546,355, the contents of which are incorporated by reference in its entirety.

In some embodiments, the flavivirus is a chimeric flavivirus, wherein the viral genome comprises a backbone of a first flavivirus (including C, NS1, NS2A, NS2B, NS3, NS4A, NS4B and NS5 genes) and the preMembrane (prM) and envelope (E) genes of a second flavivirus, wherein the second flavivirus is selected from DENV1, DENV2, DENV3 or DENV4. The first flavivirus can be a different dengue serotype or another flavivirus, such as yellow fever virus.

In certain embodiments, the flavivirus is a Dengue virus. In other embodiments, the Dengue virus is a dengue virus from one of the 4 dengue virus serotypes, referred herein as DEN1 (dengue virus serotype 1), DEN2 (dengue virus serotype 2), DEN3 (dengue virus serotype 3), or DEN4 (dengue virus serotype 4). In one embodiment, the Dengue virus comprises a viral genome that comprises a TL-2 Δ30 modification in the 3'UTR. In another embodiment, the Dengue virus is a DEN1 virus wherein the viral genome of DEN1 comprises a 30 nt deletion corresponding to the TL2 stem-loop structure in the 3' UTR (rDEN1Δ30). In another embodiment, the dengue virus is a DEN2 virus comprising the DEN2 prM and E genes on a DEN4 backbone, wherein the DEN4 backbone comprises a 30-nt deletion corresponding to the TL2 stem-loop structure in the 3' UTR (rDEN2/4Δ30). In a further embodiment, the Dengue virus is a DEN3 virus wherein the DEN3 viral genome comprises a 30 nt deletion corresponding to the TL2 stem-loop structure in the 3' UTR and a separate, noncontiguous, upstream 31 nucleotide deletion corresponding to the TL-3 structure of the 3' UTR (rDEN3 Δ30/Δ31). In an additional embodiment, the Dengue virus is a DEN4 virus, wherein the DEN4 viral genome comprises a 30 nucleotide deletion corresponding to the TL2 stem-loop structure in the 3' UTR (rDEN4Δ30).

The virus may be a primary viral isolate directly obtained from an infected individual, a genetically engineered attenuated virus, a genetically-engineered replication-deficient virus, a cell line passaged adapted virus, a cold-adapted virus, a temperature-sensitive mutant virus, or a genetically engineered re-assortant virus.

Any endonuclease used in tissue culture can be used in the methods of the invention. Endonucleases can be classified based on their substrates as follows: deoxyribonucleases (DNases) which degrade DNA, i.e., have DNA specificity; ribonucleases (RNases) which degrade RNA, i.e., have RNA specificity; and endonucleases that degrade DNA and RNA, i.e., have specificity for both DNA and RNA. Endonucleases DNases include but are not limited to DNase I, DNase II and endodeoxyribonuclease IV. Endonucleases RNases include but are not limited to RNase I, RNase III, RNAse E, RNAse F and RNAse P. One such example of an endonuclease that degrades DNA and RNA is Benzonase®, a broad spectrum endonuclease derived from the bacterium *Serratia marcescens*. See, e.g., Eaves et al., 1963, J. Bacteriol. 85:273-278. Benzonase® is a genetically engineered endonuclease which degrades both DNA and RNA strands in many forms by hydrolyzing internal phosphodiester bonds between specific nucleotides to form 5'-monophosphate terminated oligonucleotides which are 3 to 8 bases in length. It promotes quick reduction of the viscosity of cell lysates, which facilitates ultracentrifugation. It reduces proteolysis and increases the yield in targeted protein and offers complete elimination of nucleic acids from, e.g. recombinant, proteins. It has an exceptionally high activity of 400,000 U/mg.

The endonuclease, e.g. Benzonase®, is added once to the medium at a very low initial concentration of 5-500 units/ml, 10-250 units/ml or 20-80 units/ml (or as low as 2.5 U/mL; or 5 U/mL as exemplified for the Dengue vaccine) of medium. In some embodiments, the endonuclease effectively clears (to below 20 ng/ml in the supernatant) the cell culture medium of free DNA and/or RNA originating mainly from lysing or lysed host cells. In some embodiments, the amount of host cell DNA is less than 20 ng/ml as measured by qPCR. In certain embodiments, the endonuclease is added at a concentration of 2.5, 5, 7.5, 10, 12.5, 15, 20, 25, 30, 25, 40, 50, 60, 70, 80, 90, 100, 125, 150, 175, 200, 225, 250, 275, 300, 350, 400, 450 or 500 units/ml of medium.

As demonstrated in the EXAMPLES, the use, under the same conditions, of 20-80 units/ml of Benzonase® leads to a superior decrease of DNA concentration when the endonuclease is added during cell culture compared with the use of 80 units/ml Benzonase® applied post harvest, with no impact to cell growth or virus production, surprisingly also when cells are grown adherently on microcarriers.

The virus is placed in contact with the cells grown adherently on microcarriers or T-flasks (HCMV in ARPE-19 or Dengue in Vero) to allow the virus to infect the cells and to propagate. For instance, the viral seed lot is added to the cell culture and allowed to absorb on the cells, for instance, for about 30 minutes with gentle mixing (e.g., about 30 rpm), after which further culture medium may be added and the pH adjusted if desired. Stirring speed may be adjusted and the culture maintained. Following infection, amplification of the number of virus particles takes place. This step can suitably be performed in bioreactors, for instance, at scales of between 1 and 20,000 liters, e.g., between 10 and 2,000 liters, e.g., between 50 and 1,000 liters, which scale can easily be adjusted to the demand for the vaccine. In certain embodiments, the bioreactor is a single use bioreactor (SUB).

The reaction conditions within the bioreactor for activity of the endonuclease include 1) a pH between 6.0 and 9.0, preferably between 7.0 and 8.0, and more preferably a pH of 7.2; 2) a temperature between 25° C. and 45° C., preferably at a temperature comprised between 30° C. and 40° C., more preferably at a temperature comprised between 35° C. and 40° C., and even more preferably at a temperature of 37° C.; and 3) a cofactor such as $MgCl_2$ at a concentration of 2 mM. In certain embodiments, $MgCl_2$ can be used at concentrations 1.0 mM to 10 mM, or 1 mM to 5 mM. Other divalent cations such as $CaCl_2$ may be suitable for use.

In the methods of the invention where HCMV is propagated, the endonuclease is typically added to the culture media post infection, up to 8 days prior to supernatant harvest. In the methods of the invention where Dengue virus is propagated, the endonuclease is added concurrently with virus infection or just after virus infection, e.g., within 1, 2, or 3 hours post infection. The culture is permitted to proceed for up to 15 days prior to harvesting. In some embodiments where the Dengue virus is propagated, the culture is permitted to proceed for 7 days or up to 8 days prior to harvesting. In other embodiments where the Dengue virus is propagated the culture is permitted to proceed for up to 9, 10, 11, 12, 13, 14, or 15 days prior to harvesting.

The reaction conditions within the HCMV infected ARPE-19 microcarrier bioreactor for efficient activity of endonuclease have been demonstrated at 1) a pH between 6.6-7.3, 2) an endonuclease concentration of 20-80 U/mL culture, 3) a $MgCl_2$ cofactor concentration of 2 mM, and 4) a temperature between 35° C. and 39° C. Endonuclease addition time has been demonstrated post infection, from 0.5 to 8 days prior to virus product harvest, with more efficient digestion at earlier additions.

The reaction conditions within the Dengue-virus-infected Vero T-225 flasks have been demonstrated at 1) a pH between 6.8 and 7.3, 2) an endonuclease concentration of 5-20 U/mL culture, 3) a $MgCl_2$ cofactor concentration of 2 mM, and 4) a temperature of 37° C. Endonuclease addition time has been demonstrated at infection, up to 7 days prior to virus product harvest. In certain embodiments, however, endonuclease addition will occur at infection up to 15 days prior to virus product harvest. In other embodiments, the reaction conditions are for Dengue virus infected Vero microcarrier bioreactors.

After propagation of the virus in the cells, the virus or components thereof are harvested from the cell culture. This can be done by routine methods, which are known to the skilled person. The virus produced and released in the cell culture medium can be separated from the cellular biomass by conventional methods, such as clarifying filtration, centrifugation, or ultrafiltration, and harvested in the supernatant. Conventional processes for harvesting the virus can be used, for instance, those described in U.S. Pat. No. 4,525,349. In brief, the liquid medium suspension containing the virus is typically withdrawn, filtered and concentrated by, for instance, ultrafiltration. For instance, at the end of the culture, harvesting is carried out by collecting the culture medium containing the viral suspension.

The clarified harvest can optionally be ultrafiltrated to concentrate the viral suspension, and subsequently, the virus can be purified using any of several protocols known to one skilled in the art, e.g., using gel filtration and/or ion exchange chromatography, for instance, following the procedures as described in U.S. Pat. No. 4,525,349, the contents of which are incorporated herein. The resulting concentrated virus suspension can optionally be diluted, and subsequently inactivated if required, for which conventional methods can be used.

In particular preferred embodiments the virus is further processed to a split virus comprising any one of the following steps of dilution, homogenization, nuclease treatment, pressure filtration, ultra/diafiltration, solubilisation, diafiltration, chromatography, stabilization by formaldehyde treatment, dilution, ultra/diafiltration, (detergent) stabilizer addition, a second homogenisation and sterile filtration.

Methods for harvesting and purifying virus or viral components, and production of vaccines therefrom are used in the art for decades already, and thus are well known and have been amply described. See, for example, Montagnon et al., 1984, Rev Infect Dis. 6 Suppl 2:S341-4; WO 2007/007344; U.S. Pat. No. 4,525,349, all incorporated by reference herein.

Clarification of the mixture obtained allows under suitable conditions the withdrawal of the cellular debris. Clarification is preferably performed by depth filtration. Depth filtration includes but is not limited to the use of one or more commercially available products such as Sartopure® filters from Sartorius (e.g. Sartopure®), CUNO Incorporated AP series depth filters (e.g. AP01), CUNO Incorporated CP series depth filters (e.g. CP10, CP30, CP50, CP60, CP70, CP90), CUNO Incorporated HP series depth filters (e.g. HP10, HP30, HP50, HP60, HP70, HP90), CUNO Incorporated Calif series depth filters (e.g. CA10, CA30, CA50, CA60, CA70, CA90), CUNO Incorporated SP series depth filters (e.g. SP10, SP30, SP50, SP60, SP70, SP90), CUNO Delipid and Delipid Plus filters, Millipore Corporation CE series depth filters (e.g. CE15, CE20, CE25, CE30, CE35, CE40, CE45, CE50, CE70, CE75), Millipore Corporation DE series depth filters (e.g. DE25, DE30, DE35, DE40, DE45, DE50, DE55, DE560, DE65, DE70, DE75), Millipore Corporation HC filters (e.g. A1HC, B1HC, COHC), CUNO PolyNet™ Filters (e.g. PolyNet™ PB P050, P100, P200, P300, P400, P500, P700), Millipore Clarigard® and Polygard® filters, CUNO Life Assure filters, ManCel Associates depth filters (e.g. PR 12 UP, PR12, PR 5 UP); and PALL or SeitzSchenk Incorporated filters. In order to improve the clarification capacity of the available depth filtration units, it can be useful to couple two or more units with decreasing pore sizes In another preferred embodiment of the invention, concentration step is performed by ultrafiltration. According to the invention, the ultrafiltration is preferably a cross-flow filtration. The principle of cross-flow filtration is known to the person skilled in the art (see, e.g., Richards, G. P. and Goldmintz, D., J. Virol. Methods (1982), 4 (3), pages 147-153. "Evaluation of a cross-flow filtration technique for extraction of polioviruses from inoculated oyster tissue homogenates").

Diafiltration of the fraction (e.g. the retentate when the concentration step has been performed by microfiltration or by ultrafiltration) is an improvement of microfiltration and involves diluting said fraction comprising the viruses with a solution to effect a reduction in the concentration of the impurities in said fraction. The dilution of the fraction comprising the viruses allows washing out more of the impurities from said fraction. It is understood that the diafiltration may be carried out in a batch mode, semi-continuous mode, or a continuous mode. The diafiltration step can be advantageously used to change the buffer in which the virus is comprised as well as selective remove impurities by size. It can be useful to exchange the buffer used in the purification process against a pharmaceutically acceptable buffer. Filters used according to the invention are preferably amenable to sterile processing. Autoclaveable filters are commercially available such as UFP hollow fiber membranes (GE Healthcare) or Prostak Microfiltration Modules (Millipore). Gamma irradiated membranes are commercially available as well, such as RTP hollow fibers (GE Healthcare) or irradiated hollow fibers from Spectrum Labs. Diafiltration of the fraction comprising the viruses is preferably performed over filters having a pore size of ~0.1 µm.

Beyond diafiltration, chromatographic separations may be used to isolate the virus from impurities. Such separations can occur via virus bind and elute or virus flowthrough modes utilizing various types of separation, including but not exclusively, ion exchange, hydrophobic interaction, size exclusion, and multi modal ligands. Preferred chromatographic platforms include those suited for large molecules, such as monolith columns or membrane absorbers, such as those commercially available from Sartorius (Sartobine), Bia Separations (CIM monolithic columns), and Natrix Separations (Natriflo™). Resin based chromatographic platforms, such as those offered by EMD Millipore (Eshmuno®, Fractogel®), GE Healthcare (CAPTO), and Tosoh Biosciences (Toyopearl®) may also be effectively used to isolate virus from impurities.

The whole-virus vaccines prepared using the methods of the present invention may be used for the prophylactic or therapeutic treatment of viral infections. They may be administered as known in the art, e.g. intravenously, subcutaneously, intramuscularly or intranasally. The virus strains disclosed herein and the vaccines made thereof may, however, also be used as vectors or shuttles to present heterologous antigens to the immune system, e.g. antigens of viral envelope proteins such HIV-1 or hepatitis antigens.

One skilled in the art would readily appreciate that the present invention is well adapted to carry out the objects and obtain the ends and advantages mentioned, as well as those inherent therein. The methods and compositions described herein, as presently representative of preferred embodiments, are exemplary and are not intended as limitations on the scope of the invention. Changes therein and other uses will occur to those skilled in the art, which are encompassed within the spirit of the invention, are defined by the scope of the claims.

EXAMPLES

Analytical Methods
Analytical Methods to Characterize Culture Health, Virus Production, and DNA Levels for HCMV expressed in ARPE-19 Applications (Examples 1 and 2)
1. Measuring Culture Cell Count and Cell Viability via Nucleocounter®

A NucleoCounter® NC-200™ instrument (ChemoMetec Inc., Davis, Calif.) was used to measure culture cell count and viability. The instrument counted cells and cell viability of samples containing cells on microcarriers via a nuclear stain and cell lysis buffering system.

2. Measuring Culture Metabolism via BioProfile Flex

Metabolite and pH analysis of supernatant samples was performed via a BioProfile® Flex instrument (Nova Biomedical, Waltham, Mass.).

3. Measuring Sample HCMV Protein Mass by anti-HCMV ELISA

The sandwich enzyme linked immunosorbent assay (ELISA) used an anti-HCMV monoclonal antibody for capture and a polyclonal antibody for detection, with an alkaline phosphatase conjugated secondary antibody. Results are reported relative purified HCMV reference standard.

4. Measuring Sample Infectious HCMV Particles by Cell-Based Infectivity Assay:

Infectious particles were measured via a cell-based assay using human retinal epithelial cells planted in 96-well or 384-well microtiter plates. Cells were incubated for 24 hours, and then infected with serial dilutions of HCMV samples or reference standard. The infected cells were incubated for 24 hours and fixed with a dilute formaldehyde solution.

Following fixing, infection was then detected using one of two methods:
  (1) LI-COR method: Cells were incubated with the primary antibody [anti-HCMV mAb] at 2-8° C. overnight on a rotating platform. A conjugated secondary antibody [Goat anti-mouse IgG (H+L) IRDye 800CW-LI-COR] was added to the cells and finally the plates were dried and read on an Aerius™ Automated Infrared Imaging System (Li-Cor Biosciences, Lincoln, Nebr.).
  (2) % Infection Method: Cells were fluorescently stained using an anti-HCMV monoclonal antibody with an anti-species fluorophore conjugate and direct binding of Hoechst to the nuclear material. Plates were imaged for the stained nuclei and the fluorescently tagged viral protein using a BioTek Cytation™3 reader to determine the % infected cells per each well.

A dose response curve was generated from the % infection signal to calculate the potency of each sample relative to the reference standard.

5. Measuring Sample HCMV Genome Copies by Genome Quantitation Assay:

Total nucleic acids were isolated from the sample by proteinase K treatment, phenol-chloroform extraction, and alcohol precipitation. HCMV genome concentration was measured by a real-time quantitative PCR standard curve assay (standard curve range: 1E9 copies/mL-1E5 copies/mL).

6. Measuring Sample Protein Content by Bradford:

The Pierce™ 660 nm Assay (ThermoFisher Scientific Inc., Waltham, Mass.) was used to quantify total protein concentration in vaccine process intermediates and final product samples. A standard curve was prepared from Bovine Serum Albumin (BSA), and samples were diluted and incubated in the presence of Benzonase® to reduce nucleic acid interference. The Pierce™ 660 nm Assay Reagent was added, the plate was incubated at room temperature and the absorbance was read at 660 nm. Unknown sample concentrations were determined by interpolation from the standard curve using a linear fit.

7. Measuring HCMV Sample Host Cell DNA Content by qPCR:

Total nucleic acids were isolated from the sample by proteinase K treatment, phenol-chloroform extraction, and alcohol precipitation. Host cell DNA concentration was measured by a real-time quantitative PCR standard curve assay (standard curve range: 200 ng/mL-20 pg/mL).

8. Measuring Sample Overall DNA Content by PicoGreen:

Residual DNA in process samples was quantified using the Quant-iT™ PicoGreen® dsDNA kit from Life Technologies-Invitrogen™. The Quant-iT™ PicoGreen® dsDNA reagent is a fluorescent dye that selectively binds double-stranded DNA. A standard curve was prepared from the supplied λDNA standard, samples are diluted, the PicoGreen® reagent was added, and the fluorescence was measured at excitation 485 nm, emission 535 nm.

9. Measuring Benzonase Endonuclease content:

Quantitation of the DNase activity of Benzonase® in process samples was done using Amplifluor® UniPrimer II (EMD Millipore Corporation, Billerica, Mass.), a DNA hairpin substrate. A standard curve was prepared from Benzonase®, samples were diluted, the substrate was added, the plate was incubated at 37° C. for 60±5 min, and the fluorescence was measured at excitation 485 nm, emission 535 nm. The entire assay has been automated on a workstation (Tecan Systems Inc., San Jose, Calif.).

10. Measuring Virus Mass Content by Simple Western HCMV Glycoprotein Assay:

A Capillary Electrophoresis based Simple Western™ was used to monitor virus mass. The HCMV sample was reduced and denatured, then loaded to a capillary and separated by size, bound to the capillary using a photo-linking technology and probed with a rabbit HCMV glycoprotein monoclonal antibody. A goat anti-rabbit HRP conjugate secondary antibody, luminol, and peroxide were utilized for chemiluminescence detection of the HCMV glycoprotein. Virus concentration of test samples was determined relative to a purified HCMV reference standard of known virus concentration.

Analytical Methods to Characterize Culture Virus Production and DNA Levels for Dengue Expressed in Vero Cells Applications (Example 3)

1. Measuring Vero Sample Host Cell DNA Content by qPCR:

A quantitative polymerase chain reaction (qPCR) assay was used to quantify residual Vero cell DNA in samples. The residual DNA method measures residual Vero DNA using a qPCR primer-probe set specific for the target host DNA sequence. A test sample was pre-diluted as needed, and DNA was extracted from the test sample. The quantities of residual host cell DNA in the test sample were measured by interpolation against a Vero DNA standard curve.

2. Measuring Dengue Viral Genome Copies by RT-qPCR

The assay procedure was used to quantify serotype-specific virus genomes in dengue live attenuated virus vaccine samples. The assay employs reverse transcription quantitative PCR (RT-QPCR) with Dengue virus serotype-specific QPCR primers/probe sets for detection. Serotype-specific virus genome copy numbers in the test articles were determined by interpolation against standard curves of serotype-specific RNA transcripts.

3. Measuring Infectivity in Dengue Live Attenuated Virus Samples by Cell-Based Infectivity Assay Infectivity was measured via a cell-based assay using Vero (African Green Monkey kidney) cells planted in 96-well microtiter plates. Cells were incubated for 24 hours, and then infected with serial dilutions of Dengue samples or reference standard. The infected cells were incubated and then fixed with a dilute formaldehyde solution. Following fixing, cells were permeabilized using a 1% Triton X-100 solution and then incubated with the primary antibody [rabbit anti-DEN mAb] specific for the serotype being tested at 2-8° C. overnight on a rotating platform. A conjugated secondary antibody [Goat anti-mouse IgG (H+L) IRDye 800CW-LI-COR] was added to the cells and finally the plates were dried and read on an Odyssey™ Automated Infrared Imaging System (Li-Cor Biosciences, Lincoln, Nebr.). Determination of relative potency of each sample (relative to Dengue reference standard) using a 4-parameter fit parallel-line analysis was performed using SoftMax Pro (Molecular Devices).

Example 1: Comparison of Benzonase® Digestion in 125 ML Spinner Flask Cell Culture Systems Vs. Post-harvest Benzonase® Digestion Methods 1. Seeding of Spinner Flasks ARPE-19 cells (ATCC No. CRL-2302, American Type Culture Collection, Manassas, Va.) were initially cultured in static vessels (i.e., T-225 Flask). Through cell expansion, cells were eventually cultured on microcarriers in a SOL stirred tank bioreactor. Upon appropriate cell growth in the SOL reactor, the cell culture was infected with HCMV. During virus production, material from the SOL microcarrier culture was sampled and dispensed into 125 mL disposable spinner flasks (Corning, Cat. No. 3152). Throughout the following operations, the spinner cultures were maintained in an incubator at 37° C. and 5% $CO_2$ under stirred base agitation, with exception to sampling and operations post harvest.

2. Benzonase® Digestion in Spinner Flask Cultures 2.1. Addition of Benzonase® and $MgCl_2$ to Spinners After seeding the spinner flasks, Benzonase® and $MgCl_2$ were added to three of the four spinner flasks (Arms A1-A3). Specifically, a stock Benzonase® solution consisting of Benzonase® endonuclease (EMD Millipore, Billerica, Mass., Cat. No. 1.01697.0010) diluted in culture media to 12,500 Units Benzonase® (U)/mL solution was added to the three spinner flask arms, A1, A2, and A3 to bring the culture concentration to 20, 40, and 80 U/mL Benzonase® respectively. Immediately following Benzonase® addition, 1 M $MgCl_2$ stock solution was added to all four arms (A1-A3, C) to bring the culture concentration to 2 mM $MgCl_2$. Benzonase® addition to the spinner flasks occurred 8 days prior to supernatant harvest.

2.2. Sampling of Spinner Flasks

Throughout the virus production stage (8 days prior to harvest and onwards) supernatant was periodically sampled and analyzed via on demand assays or aliquotted and frozen for later analytical characterization. On demand assays included measurements of cell count and viability by NucleoCounter®, supernatant metabolites via Bioprofile®, and cell imaging via brightfield microscopy. Prior to freezing any sample, microcarriers were removed via a sieve, and whole cells were removed via syringe filtration (Pall Corporation, Port Washington, N.Y., Cat. No. 4190). In addition, sucrose was added to the sample as a cryoprotectant.

2.3. Spinner Flask Harvest and Clarification

On harvest day, the contents of the four spinner flasks were filtered separately across 0.8 μm vacuum filters (ThermoFisher Scientific, Cat. No. 125-0080). All four filtered bulks (Arm A1-A3, Arm C Clarified Bulk) were subsequently sampled for characterization.

3. Post-harvest Benzonase Digestion

After clarification and sampling of the spinner flask that had previously had no Benzonase® added (Arm C), 50 mL of the clarified bulk was treated with 80 U/mL Benzonase® and 2 mM $MgCl_2$ for 2 hrs at room temperature while agitating via a stir bar. Specifically, a stock Benzonase® solution consisting of Benzonase® endonuclease (EMD Millipore, Billerica, Mass., Cat. No. 1.01697.0010) diluted in culture media to 12,500 Units Benzonase® (U)/mL and 1 M $MgCl_2$ (Merck BSO, Cat 17RCM909) were added separately to achieve the desired concentrations. After the 2 hr incubation with Benzonase® and $MgCl_2$, the Benzonase® treated material (Arm C Benzonase® Bulk) was sampled for analysis.

Results

A: Spinner Flask Culture Progression (Cell Health, Metabolism, Virus and Protein Production)

Cell viability over the course of the spinner cultures (8 days prior to harvest and onwards) as measured by NucleoCounter® trended similarly for all four arms, indicating the addition of 20, 40, or 80 U/mL Benzonase® to the culture did not impact cell viability (FIG. 1). In addition, glucose and glutamine consumption, lactate production, and culture pH trended similarly for all four arms, indicating cell metabolism was not impacted by the presence of 20, 40, or 80 U/mL Benzonase® (FIGS. 2A-2D).

Figure 3A:
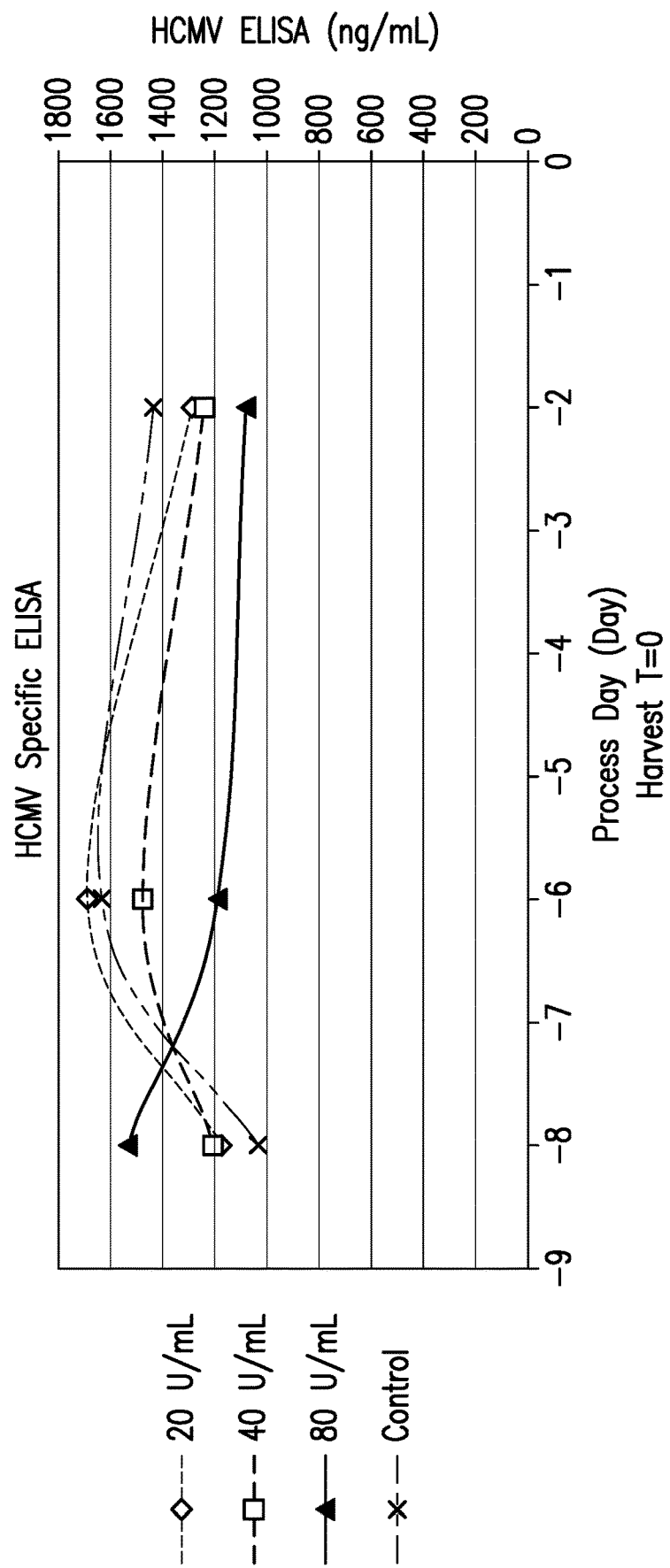
FIGS. 3A-C are plots of various indicators of HCMV virus production (A: HCMV-specific ELISA; B: qPCR for viral genomes; C: Relative Infectivity) in ARPE-19 cells grown adherently on microcarriers over time before supernatant harvest.
Figure 3B:
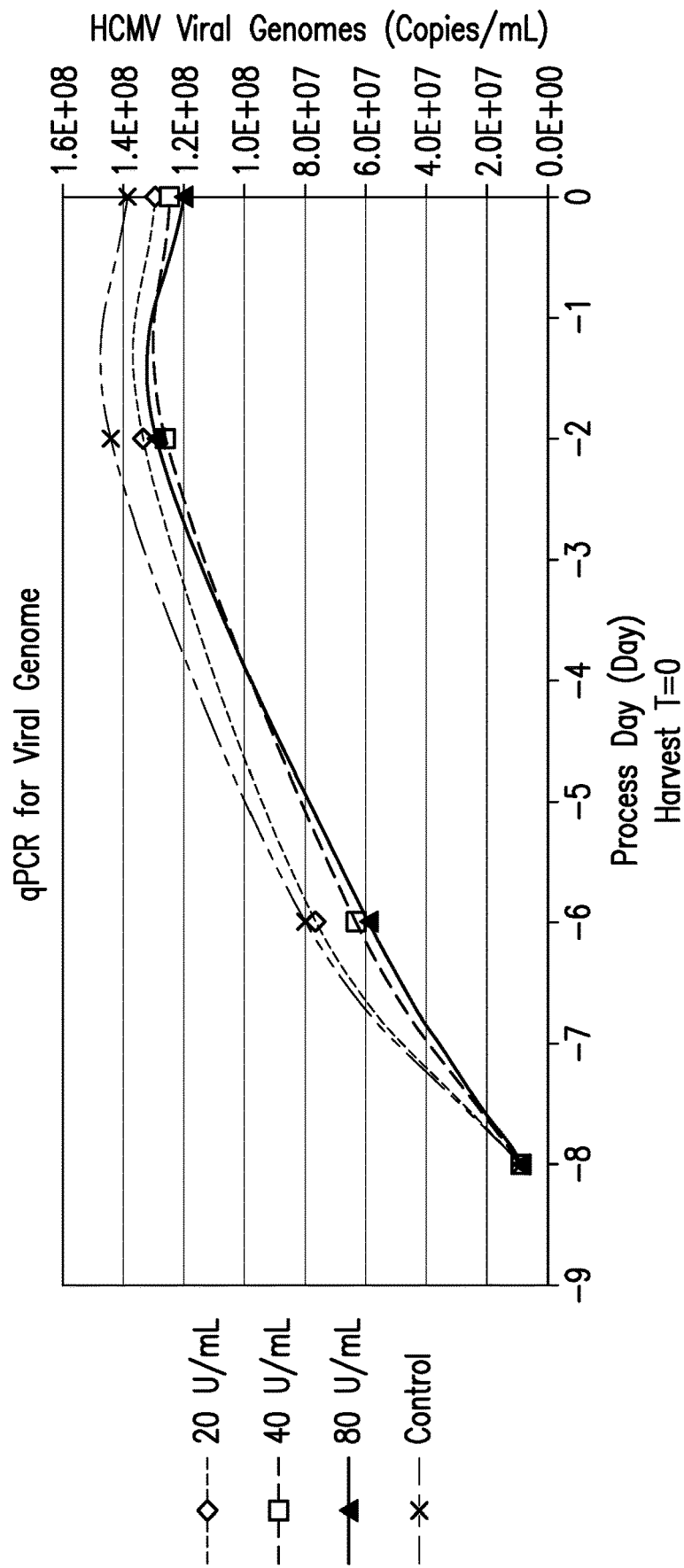
Figure 3C:
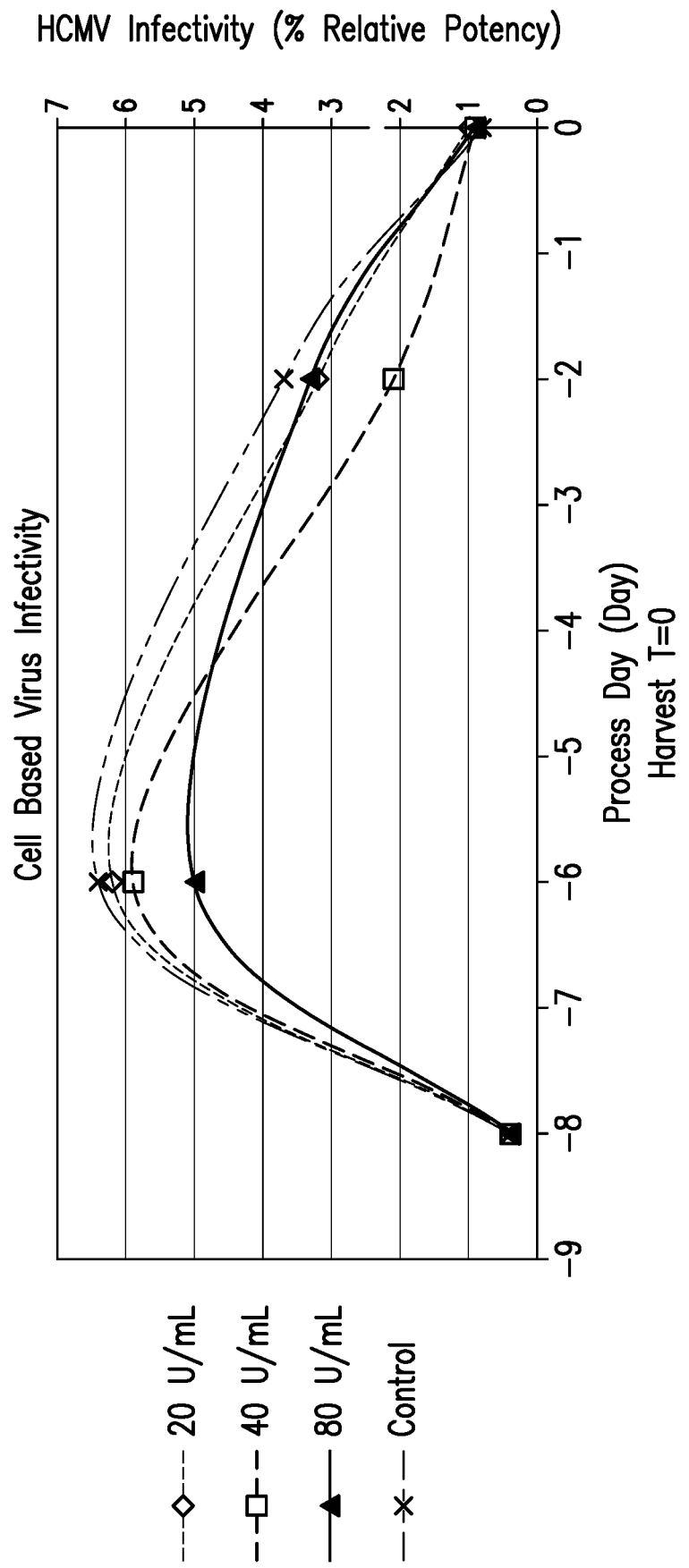
Figure 4:
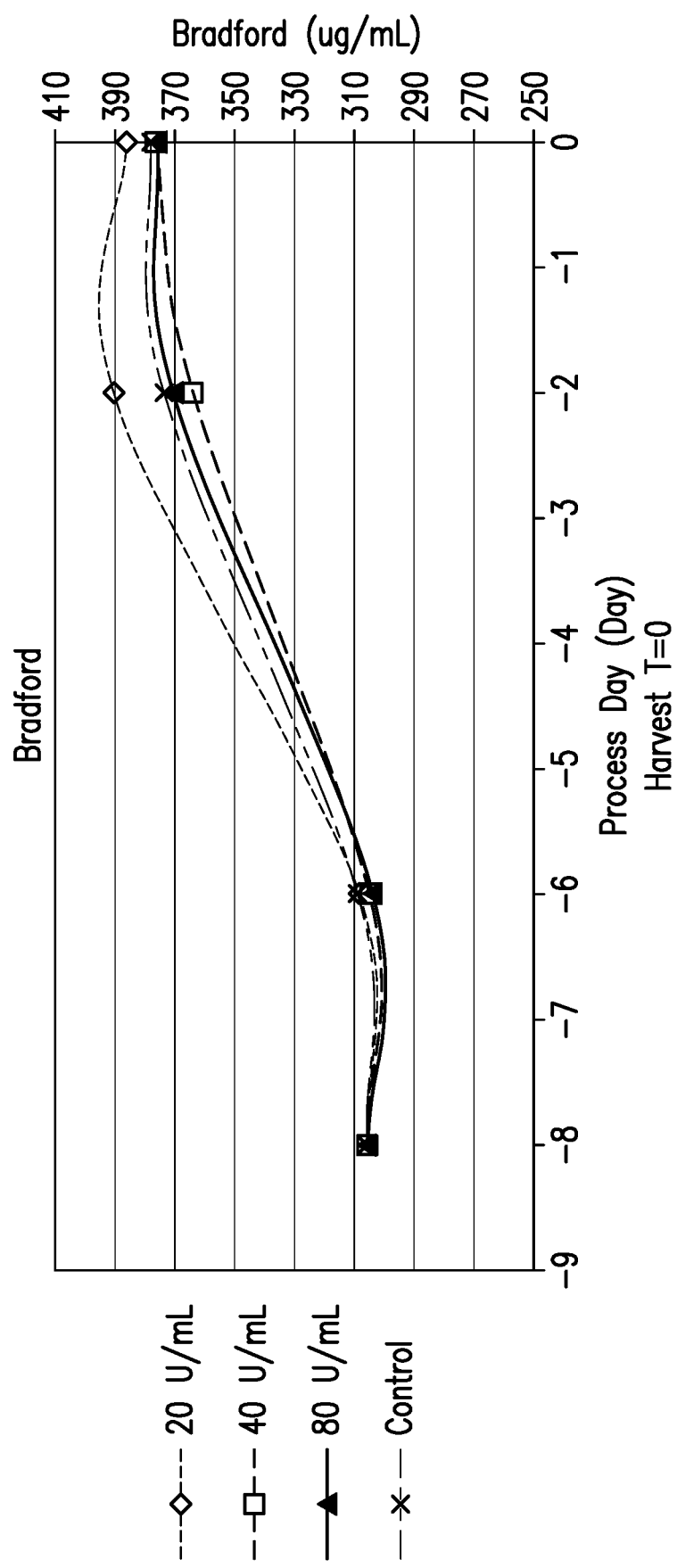
FIG. 4 is a plot of protein concentration in HCMV-infected ARPE-19 culture (as measured by the Bradford assay) grown adherently on microcarriers over time before supernatant harvest.

HCMV virus production was analyzed over the course of the spinner cultures via HCMV ELISA, Infectivity, and qPCR for viral genomes. All three measures trended similarly over all four arms, indicating virus production and stability was not impacted by the presence of 20, 40, or 80 U/mL Benzonase® (FIGS. 3A-3C). Similarly, overall protein level in the culture supernatant was not impacted; indicating overall supernatant protein content was not impacted by the presence of 20, 40, or 80 U/mL Benzonase® (FIG. 4).

B. Host Cell DNA Digestion during Spinner Culture (HcDNA Content during Virus Production)

Figure 5A:
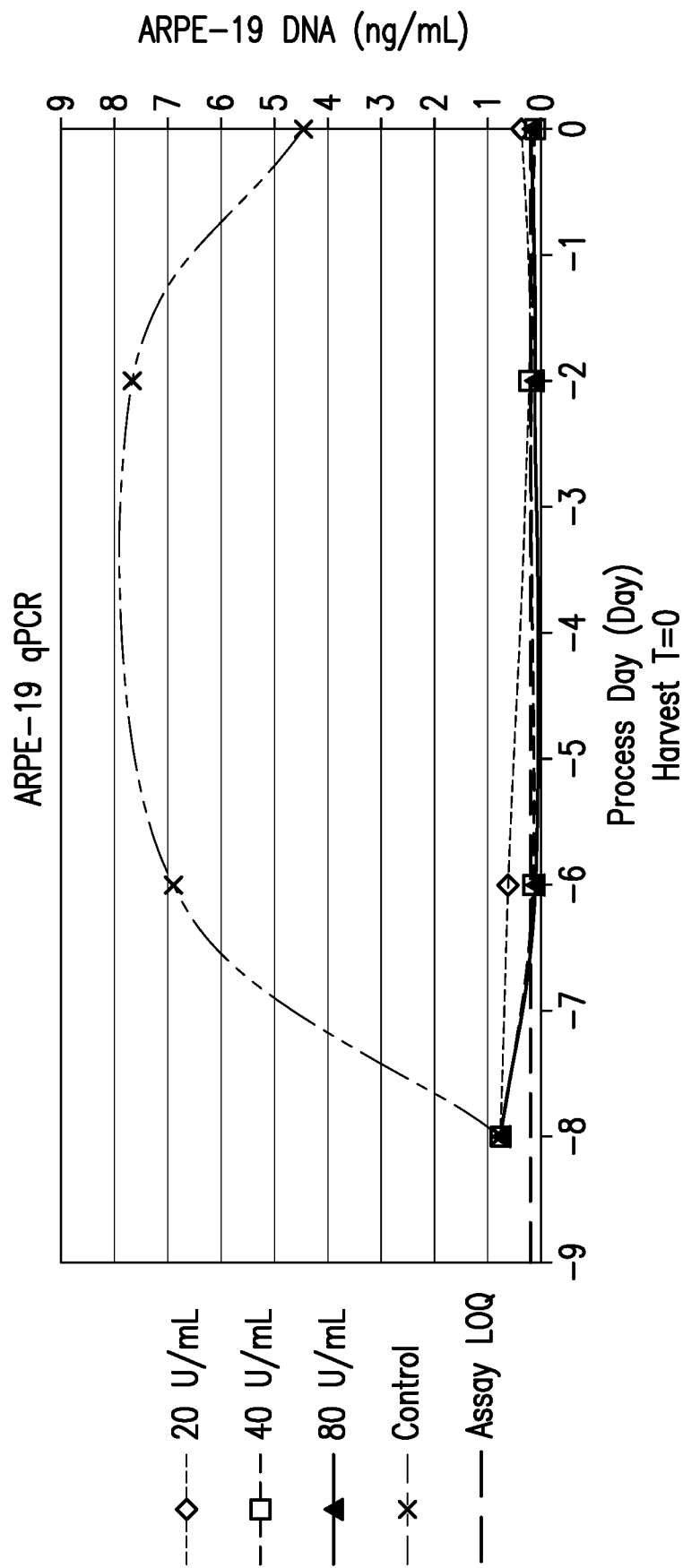
FIGS. 5A-B are plots of ARPE-19 host cell DNA in cell free supernatants (as measured by quantitative PCR) over time before supernatant harvest.
Figure 5B:
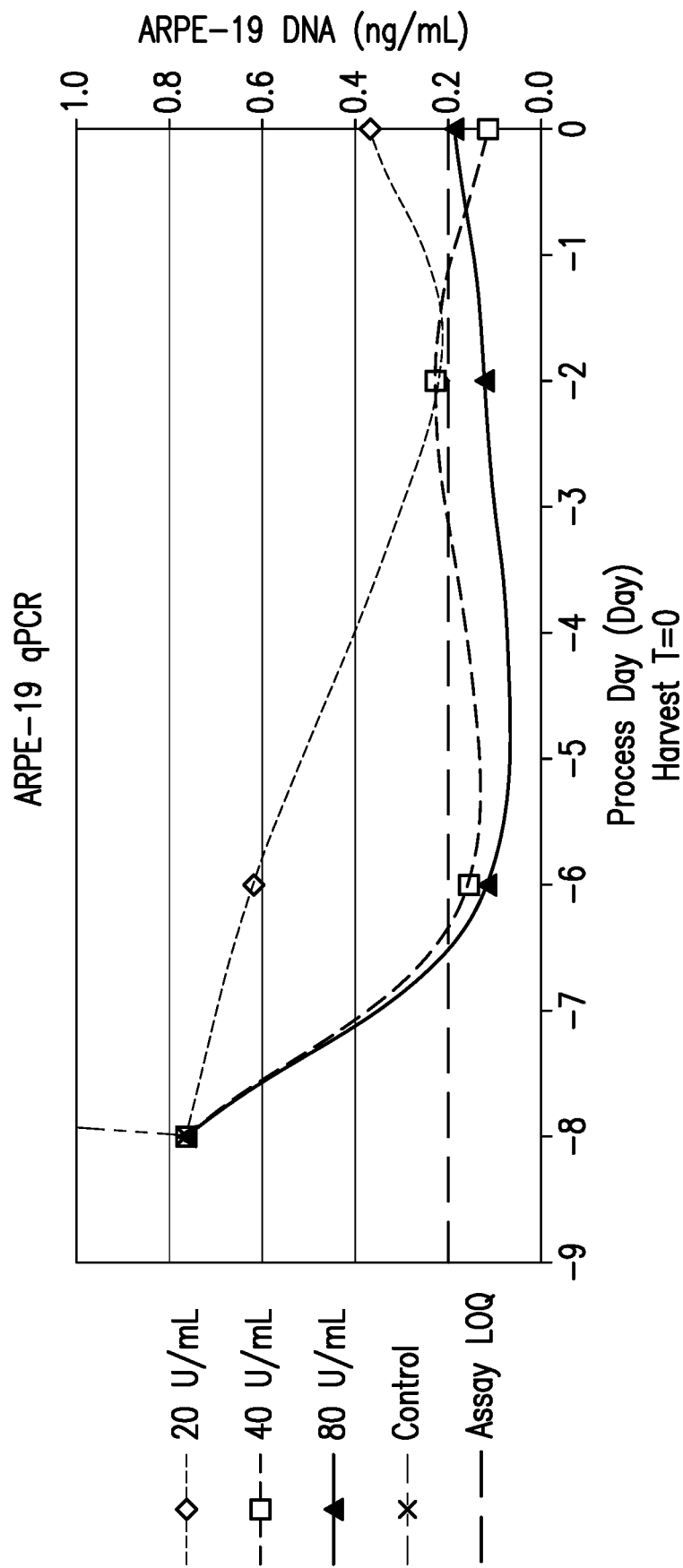
Figure 6:
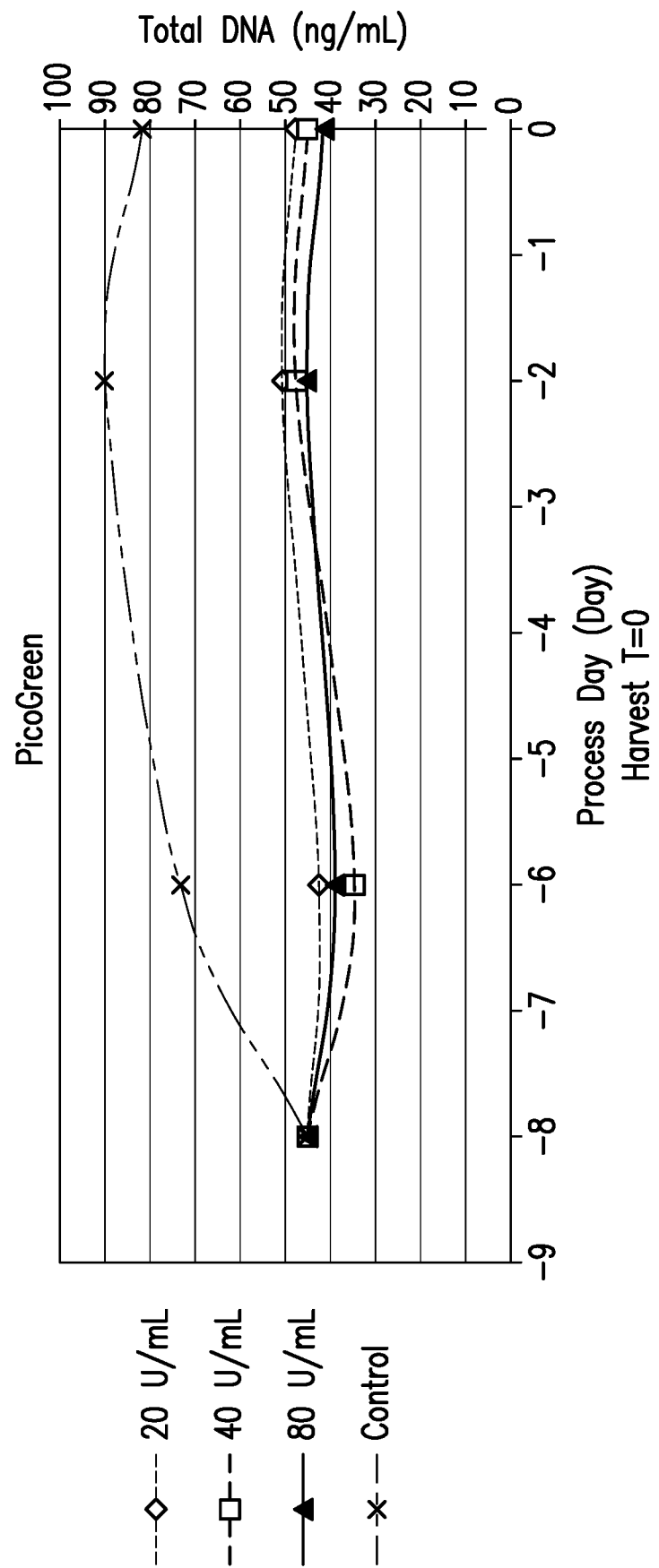
FIG. 6 is a plot of DNA concentration in cell free supernatants (as measured by the PicoGreen assay) over time before supernatant harvest.

Host cell qPCR revealed Host cell DNA increased in the culture supernatant of the spinner containing no Benzonase® (Arm C) from day 8 prior to harvest to day 2 prior to harvest. In contrast, the spinners containing 20, 40, or 80 U/mL Benzonase® (Arm A1-A3 respectively) demonstrated overall decreasing (or below LOQ [Level of Quantitation]) values over the same time. On the day of harvest, all spinners containing Benzonase® contained >10 fold less host cell DNA than the non Benzonase spinner. This data clearly demonstrates Benzonase® is effective at digesting host cell DNA in the culture supernatant over the progression (up to 8 days) of an infected culture (FIG. 5A) in a microcarrier system. While the 20 U/mL Benzonase® condition (Arm A-1) showed higher HcDNA than the 40 and 80 U/mL spinners (Arm A2-A3) 6 days prior to harvest, it reached similar levels as the culture progressed to 2 days prior to harvest (FIG. 5B), implying lower concentrations of Benzonase® may yet be effective if added early in the culture. As an orthogonal measure of DNA, PicoGreen substantiates these conclusions, exhibiting similar trends (FIG. 6). Note, a residual level of DNA is consistently maintained in the PicoGreen assay. This is likely the enveloped viral DNA, which is protected from the Benzonase®.

Figure 7:
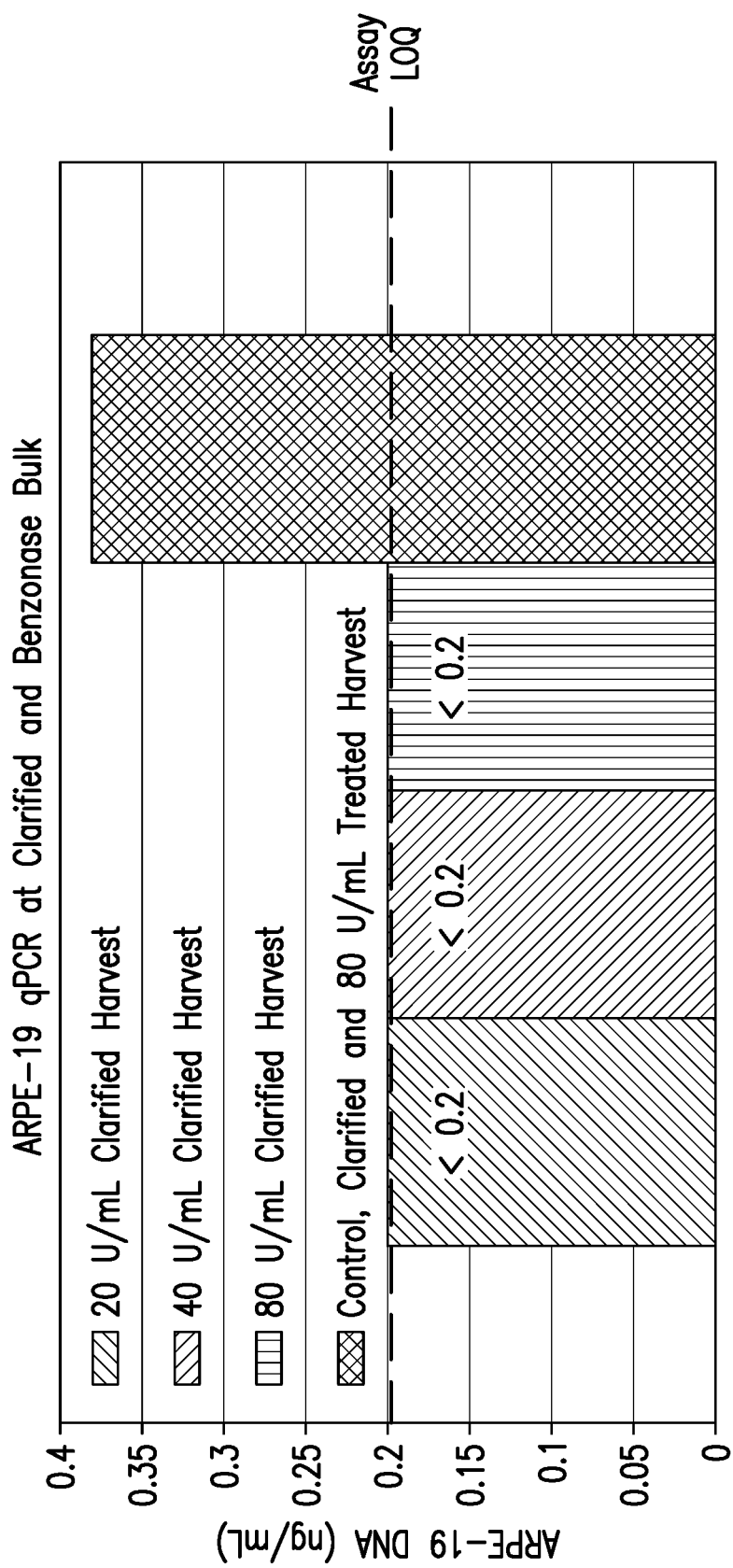
FIG. 7 is a plot of ARPE-19 host cell DNA in cell free supernatants (as measured by quantitative PCR) in HCMV spinner flasks post-harvest with varying concentrations of Benzonase® added either 8 days prior to supernatant harvest (experimental arms) or post harvest and post clarification for 2 hrs (control).
Figure 8:
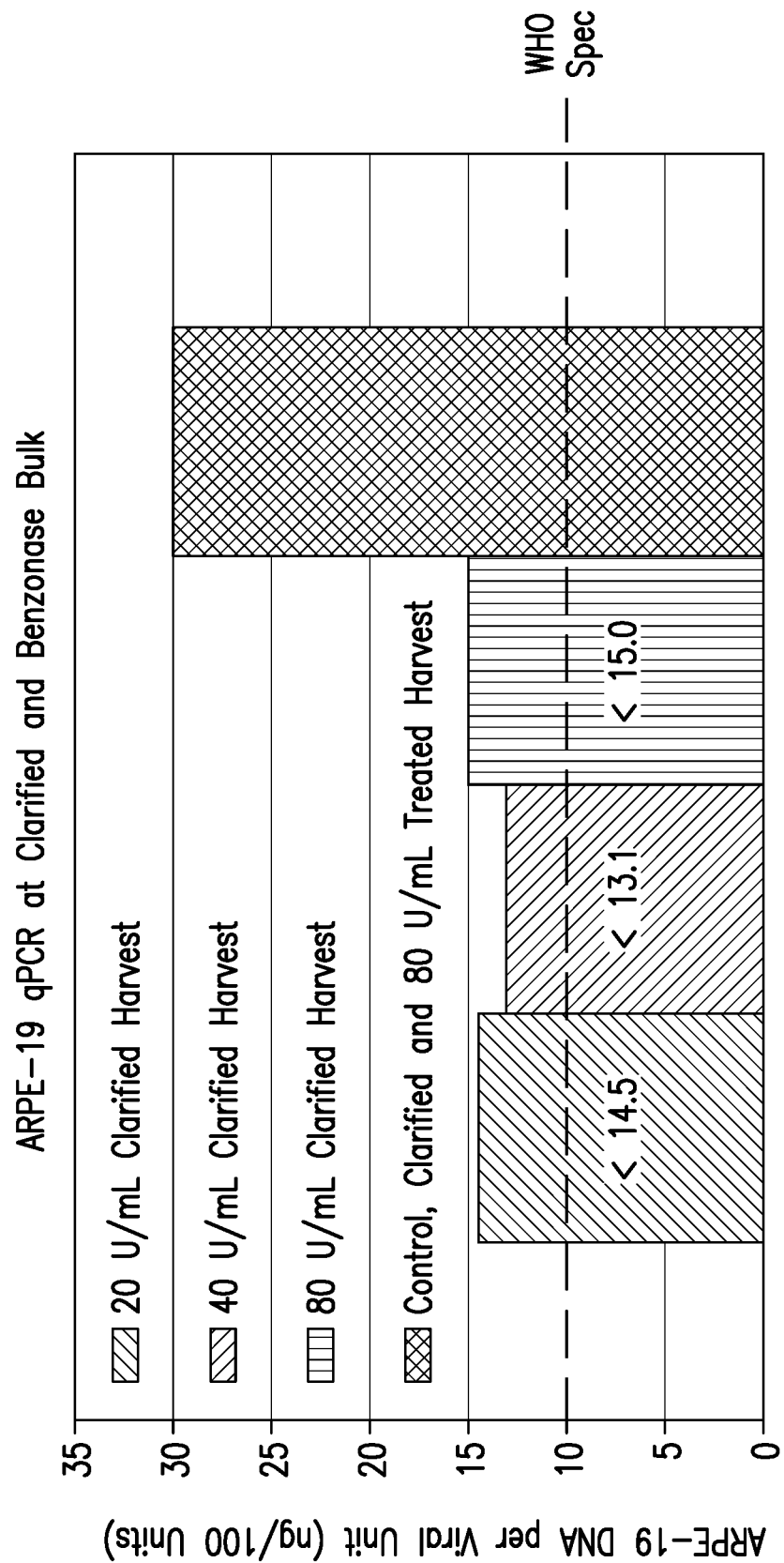
FIG. 8 is a plot of ARPE-19 host cell DNA in cell free supernatants (as measured by quantitative PCR) in HCMV infected spinner flasks post-harvest with varying concentrations of Benzonase® added either 8 days prior to supernatant harvest (experimental arms) or post harvest and post clarification for 2 hrs (control) normalized to virus dose of 100 units.

C. Comparison of Benzonase Digestion Efficiency based on Assessment of Residual Host Cell DNA after Downstream Benzonase® Digestion; Comparing Benzonase® Treatment during Culture to Benzonase® Treatment post Harvest The host cell DNA content of the clarified harvests from the three spinners containing Benzonase® (Arm A1-A3) was >1.9 fold less than that of the Benzonase® treated clarified harvest from the spinner not containing Benzonase® during culture (Arm C) (FIG. 7). This indicates that equivalent or better DNA digestion can be achieved by adding Benzonase® to the culture as compared to a post-harvest digestion (2 hr Room Temp, 80 U/mL), even if the digestion post harvest contained up to 4× more Benzonase® than that used in the culture. Furthermore, when viewing this data in the context of the WHO guidance of <10 ng HcDNA/Dose, all three spinners with Benzonase® added to the culture came in closer too and potentially within this specification (data below LOQ), without any additional purification, presenting a practical benefit to implementing Benzonase® digestion during culture (FIG. 8).

Conclusions

These data along with the trends in host cell DNA content during culture (Section B), presents an example of the benefit of HcDNA digestion that can be realized by adding nuclease, e.g. Benzonase®, to the culture of ARPE-19 cells on microcarriers compared to performing an additional post-harvest digestion. Furthermore, depending on the timing of Benzonase® addition, culture progression, and post-harvest incubation conditions, lower levels of HcDNA can be achieved in the vaccine product while using 4-fold less Benzonase®. In large part, this benefit is realized by leveraging the longer incubation time of the culture process compared to the post-harvest unit operation, with no detriment to the cell culture and virus production. While the post-harvest condition is shorter (2 hr at RT) and therefore not equivalent to the upstream addition conditions, a logistical benefit is still realized in that no downstream incubation has to take place when adding Benzonase® during the upstream culture. As such, process efficiency is gained as a Benzonase® unit operation, with associated process time and equipment, is not required in the purification process. Moreover, this may present a product quality advantage when working with unstable products that can degrade throughout downstream purification processing time.

Example 2: Comparison of Benzonase® Digestion in 3 L Bioreactor Cell Culture Systems vs. Post-Harvest Benzonase® Digestion Methods 1. Infection of 3 L Reactor Systems ARPE-19 cells were expanded and planted into sixteen 3 L reactor systems containing microcarriers through a process similar to that described in Example 1. After appropriate cell growth in the 3 L reactors, the reactors were infected with HCMV. In this experiment, a pairwise comparison of Benzonase® addition during the culture or post harvest was made under eight different experimental conditions that varied with respect to cell culture conditions.

2. Benzonase® Digestion in 3 L Reactor Systems 2.1. Addition of Benzonase® and $MgCl_2$ to 3 L Reactors With 8 pairs of duplicate reactor conditions, eight in-culture Benzonase® treated conditions could be tested against the post-harvest Benzonase® condition for the respective duplicate reactor. Accordingly, four reactor pairs were treated with 80 U/mL Benzonase® and four other pairs with 20 U/mL Benzonase® (+2 mM $MgCl_2$)) one day prior to harvest. More specifically, a stock Benzonase® solution consisting of Benzonase® endonuclease diluted in culture media to 15,000 Units Benzonase® (U)/mL solution was added to eight of the 3 L reactor systems, with four at 80 U/mL Benzonase® and four at 20 U/mL Benzonase®. Immediately following Benzonase® addition, 0.1M $MgCl_2$ stock solution was added to all eight reactors to bring the culture concentration to 2 mM $MgCl_2$.

2.2 1 day pre-Harvest vs. Post-harvest Benzonase® Digestion

On harvest day, 100 mLs of each reactor was sampled and filtered separately across 0.8 μm vacuum filters (Thermo Fisher Scientific, Cat. No. 125-0080). All 16 filtered bulks were subsequently sampled for characterization.

After clarification of the harvest samples, the samples from tanks that had previously had no Benzonase® added were treated with 80 U/mL Benzonase® and 2 mM $MgCl_2$ for 2 hrs at room temperature. Specifically, Benzonase® endonuclease at 250,000 Units Benzonase® (U)/mL and 1 M $MgCl_2$ (Merck BSO, Cat 17RCM909) were added separately to achieve the desired concentrations. After the 2 hr incubation with Benzonase® and $MgCl_2$, the Benzonase® treated material was sampled for analysis.

2.3 Sampling of 3 L Reactor Systems

One day before harvest and on harvest day supernatant was sampled and analyzed via on demand assays or aliquoted and frozen for later analytical characterization. On demand assays included measurements of cell count and viability via nucleo staining (Nucleocounter®) and supernatant metabolites via Bioprofile® (Nova Biomedical). Prior to freezing any sample, microcarriers were removed via a sieve, and whole cells were removed via syringe filtration (Pall Corporation, Cat. No. 4190). In addition, 60% (w/v) sucrose was added to the sample as a cryoprotectant to a final concentration of 10% sucrose.

Results

A. HcDNA Content in Reactor Pairs Prior to Benzonase® Addition

Figure 9A:
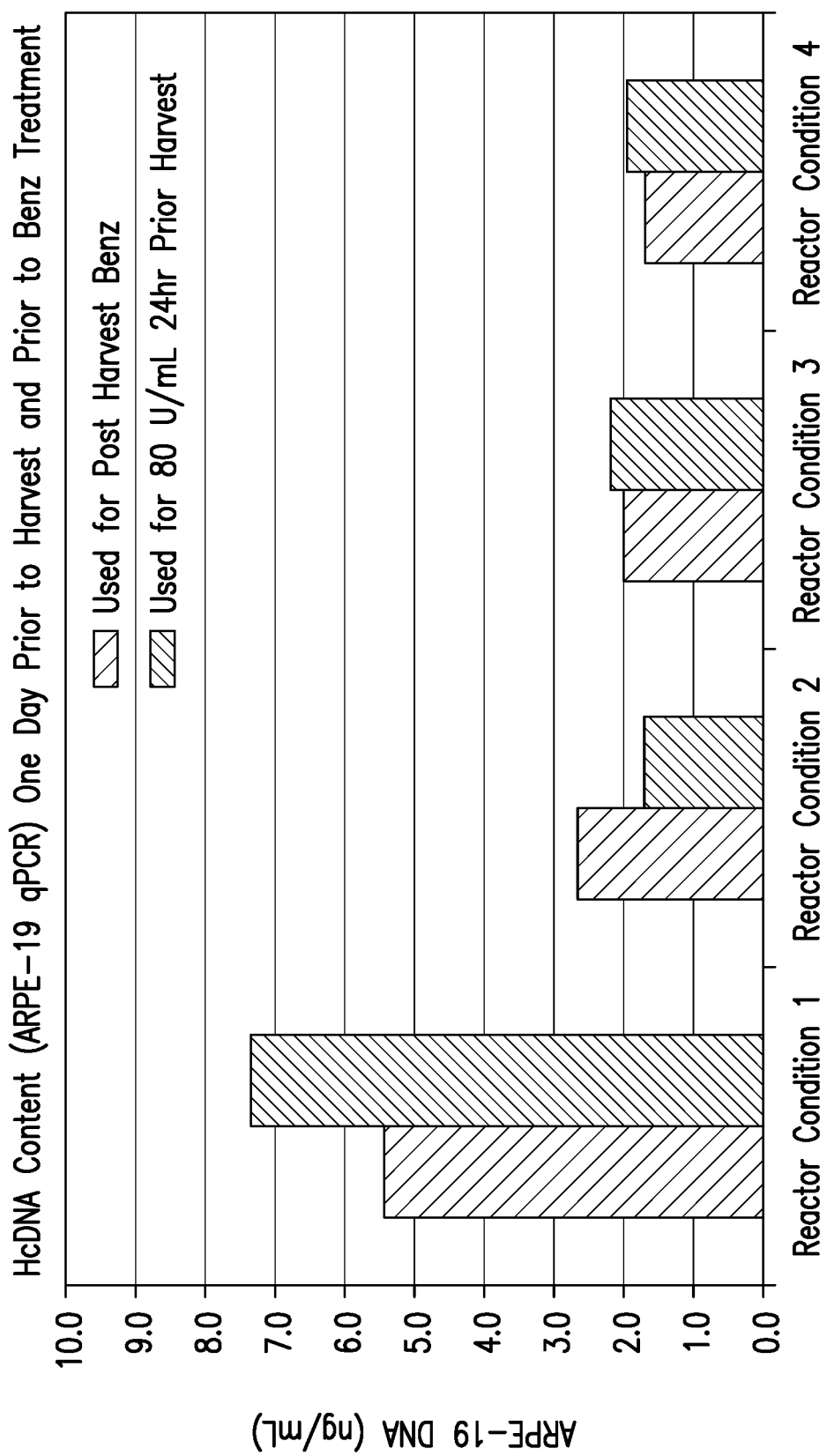
FIGS. 9A-B are plots of ARPE-19 host cell DNA in cell free supernatants (as measured by quantitative PCR) in 3 L reactor pairs on the day before harvest just prior to Benzonase® addition (A: reactor conditions 1-4; B: reactor conditions 5-8).
Figure 9B:
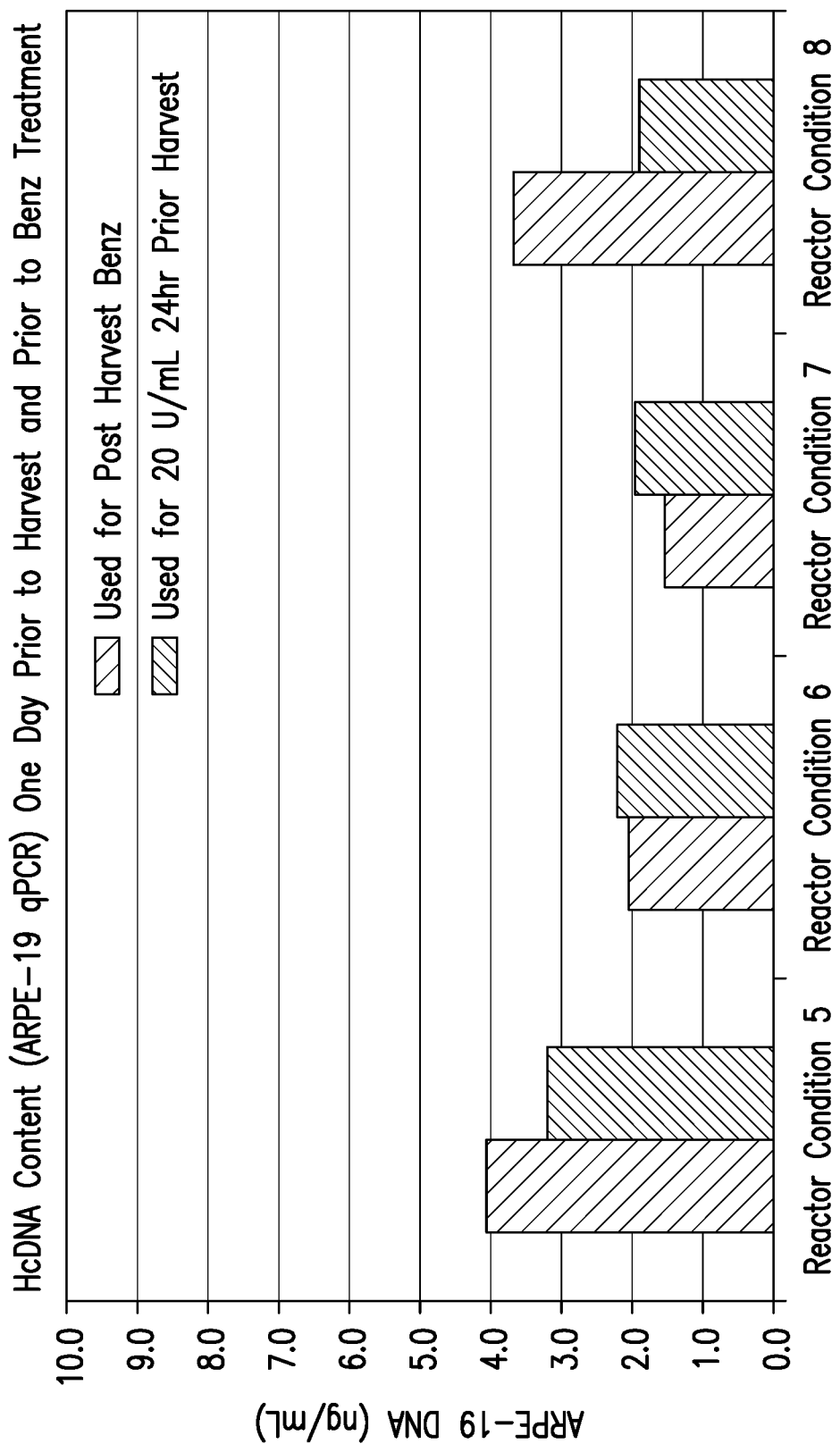

Prior to Benzonase® addition the day prior to harvest, a sample was taken from each reactor and submitted for HcDNA analysis via qPCR. The results indicate that the reactor pairs performed similarly regarding their virus production and release of HcDNA in the culture supernatant, such that comparison of DNA digestion within each reactor pair is relevant (FIGS. 9A-B). If HcDNA levels had been different between reactors in the same paired reactor condition, then assessing the final level of DNA after Benzonase® addition would have been convoluted by different amount of HcDNA in the feeds.

B. Comparison of HcDNA Content in Response to Benzonase® Conditions

Figure 10A:
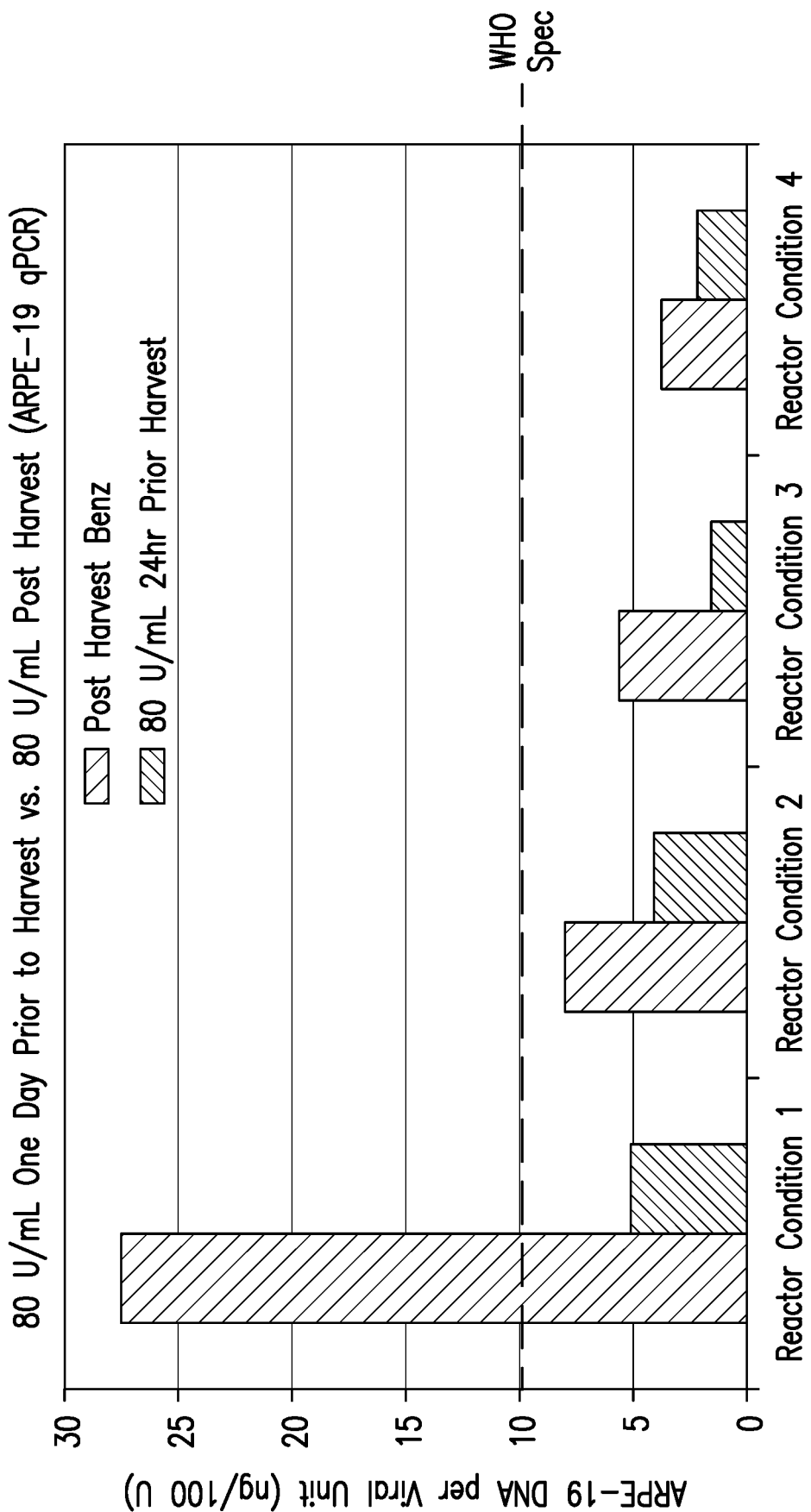
FIGS. 10A-B are plots of ARPE-19 host cell DNA in cell free supernatants (as measured by quantitative PCR) in 3 L reactor pairs post harvest and post clarification, and in the case of the control arms, post 2 hr Benzonase® incubation after clarification (A: reactor conditions 1-4, 80 U/ml; B: reactor conditions 5-8, 20 U/ml).
Figure 10B:
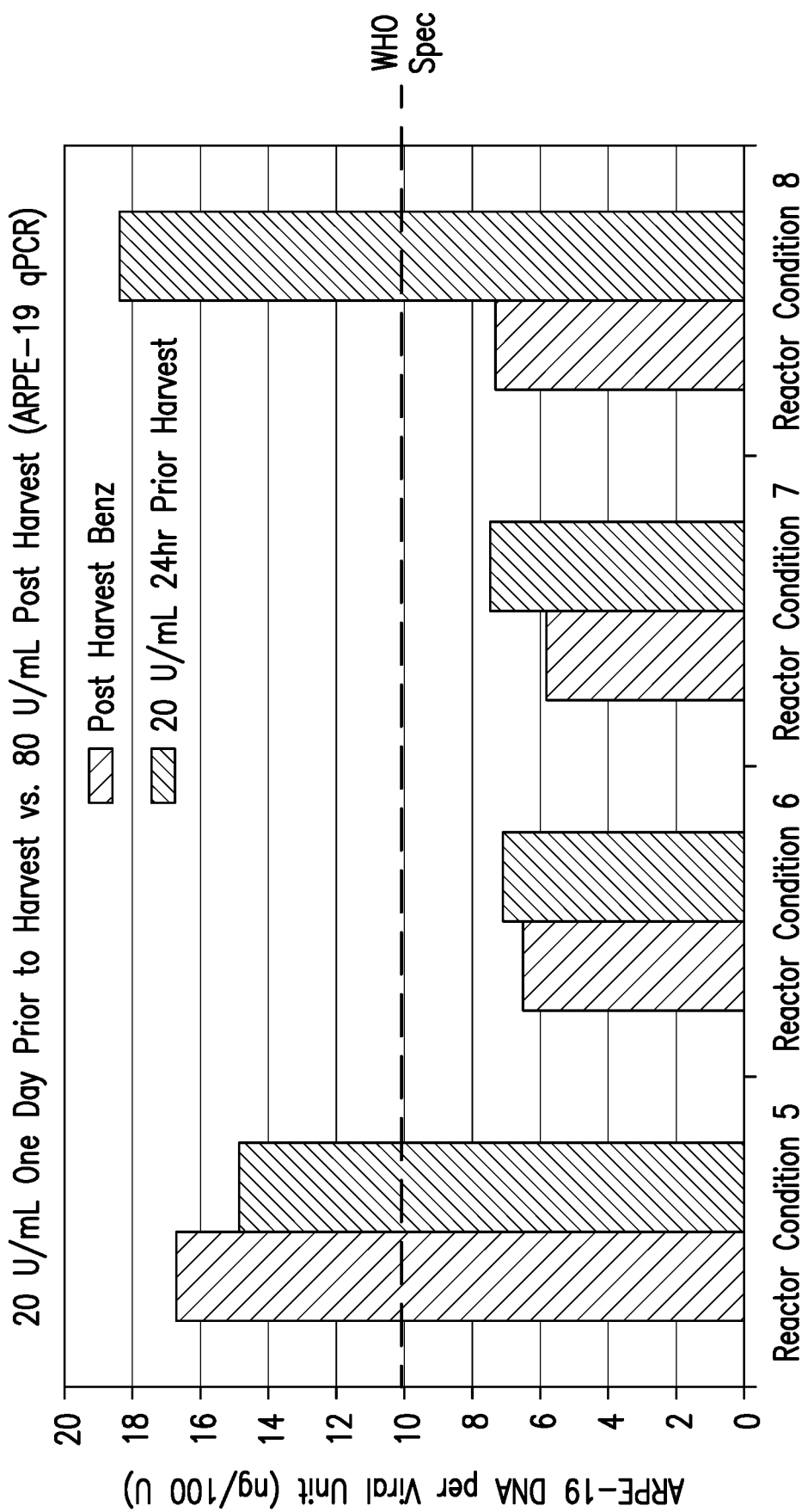

The clarified sample on harvest day from all four reactors that received 80 U/mL Benzonase® 24 hrs prior to harvest had lower HcDNA content than the associated paired reactor sample that had been treated with 80 U/mL post harvest, i.e., clarified and Benzonase® treated at 80 U/mL for 2 hrs at room temp. The clarified sample on harvest day from the four reactors that received 20 U/mL Benzonase® 24 hr prior to harvest had similar HcDNA content to the associated paired reactors that had been treated post harvest, i.e., clarified and Benzonase® treated at 80 U/mL for 2 hrs at room temp. The HcDNA content was <10 ng/dose in all four reactors that received 80 U/mL Benzonase® 24 hrs prior to harvest. The same was not true for the 20 U/mL-treated and untreated bioreactors) (FIGS. 10A-B).

C. Comparison of Viral Content of Benzonase Treated Products

Figure 11A:
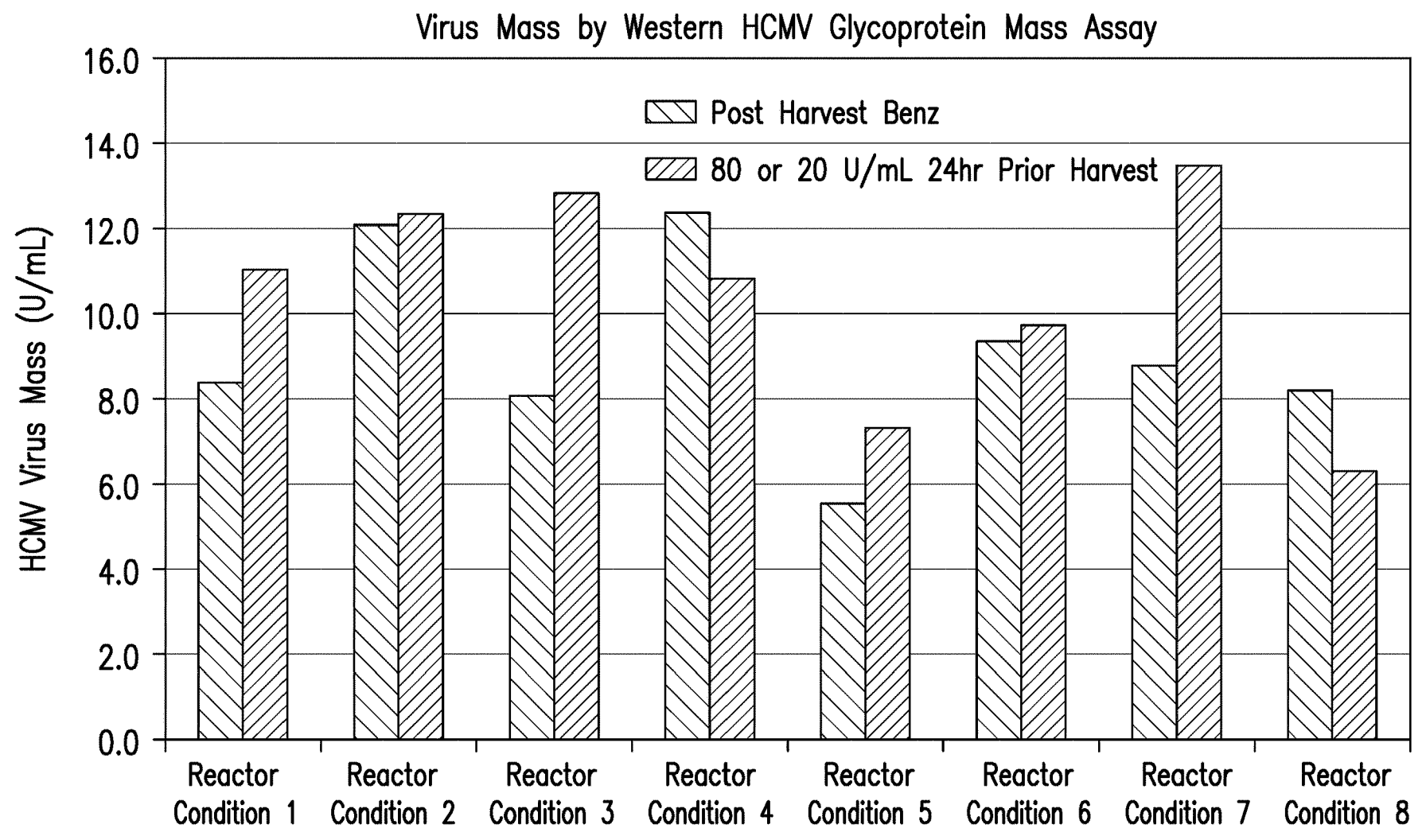
Figure 11B:
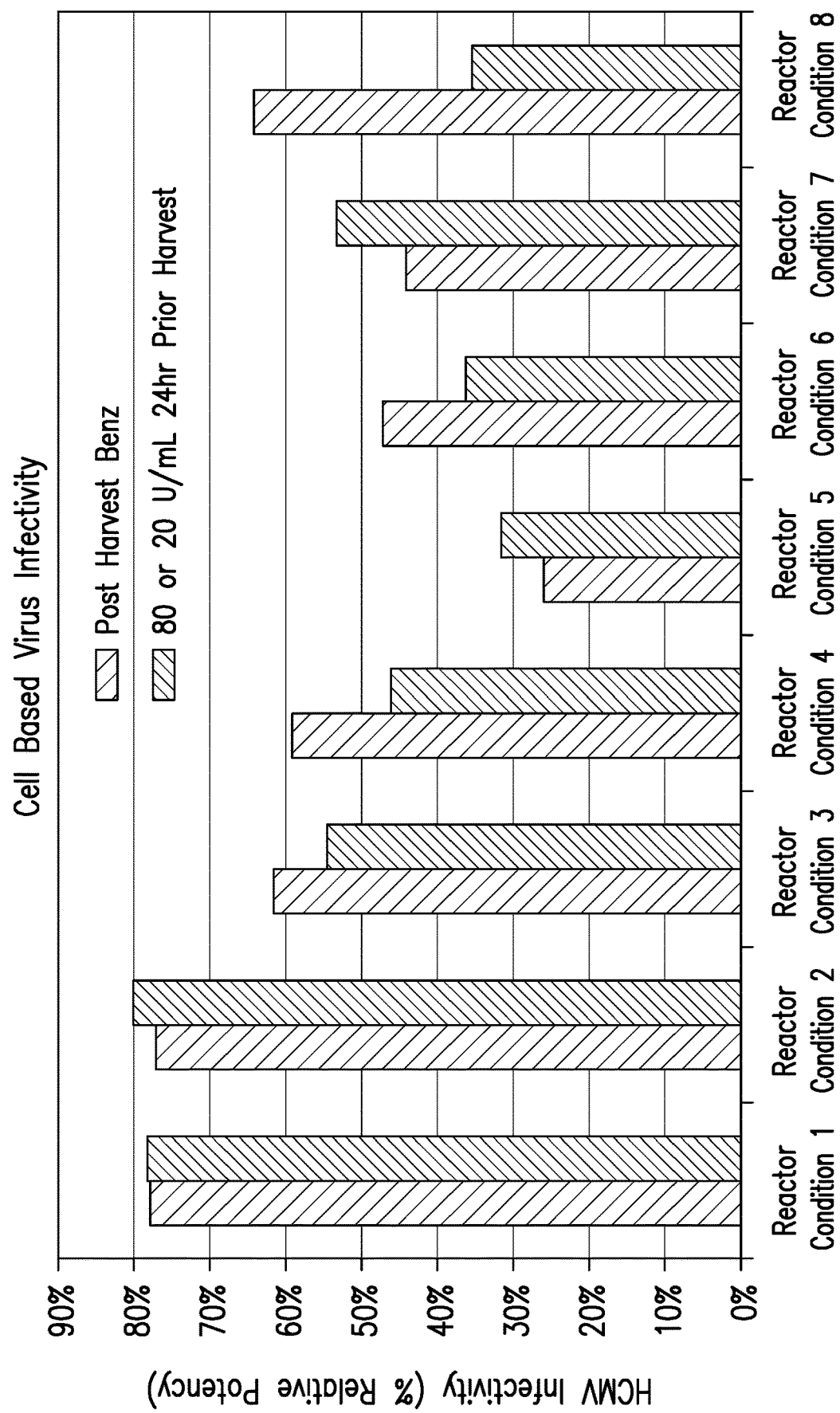

The virus content in the harvest day clarified samples from the reactors that received 20 U/mL or 80 U/mL Benzonase® 24 hrs prior to harvest was compared to the associated paired reactors that received 80 U/mL Benzonase® for 2 hrs at room temp post clarification. No detrimental trends were observed that would indicate that adding Benzonase® to a cell culture grown adherently on microcarriers prior to harvest negatively impacts the quantity, infectivity, and stability of the recovered virus. Virus mass was measured by the Western HCMV Glycoprotein Mass assay and viral infectivity by the cell based infectivity assay (FIGS. 11A-B).

Conclusions

The above results again present a practical benefit to implementing a Benzonase® digestion step during the culture process on microcarriers (in this case a 3 L culture process), even when the Benzonase® addition is only 24 hrs prior to harvest. For the 80 U/mL Benzonase® treated bioreactor conditions, the WHO recommended release spec of 10 ng/dose (N=4 of 4) was achieved, while only 3 of the 4 post-harvest treated reactors did (N=3 of 4), thereby improving process robustness in meeting the WHO guided release specs for DNA.

The fact that the reactors that received 20 U/mL 24 hrs prior to harvest displayed increased or similar levels of HcDNA reduction to their paired post-harvest treated reactors indicates the potential to reduce Benzonase® concentration and still achieve equivalent DNA reduction. As observed in Example 1, further DNA reduction is possible by the earlier addition of Benzonase® to the cell culture.

Example 3: Benzonase® Digestion with Dengue Vaccine Candidate

Methods

Vero cells were cultured on T-225 flasks and expanded until 14 flasks of confluent cells were attained. Upon confluence, the flasks were split into four different arms. Experimental arms included the addition of Benzonase® (added to the infection media containing Dengue), at concentrations of 5, 10, or 20 U/mL. The control arm was not treated with Benzonase®. The four arms (control, 5, 10, 20 U/mL Benzonase®) were run in triplicate, for a total of 12 flasks. The two remaining flasks of the original 14 were sacrificed at this point to attain a cell count just prior to infection.

After infection via media exchange with infection media, all 12 T-225 flasks were incubated for 7 days as per the virus production process. At day 7 post infection, all 12 flasks were harvested and processed through a downstream process in parallel (each flask separate). The downstream process included post-harvest Benzonase® addition (control flasks only) at 20 U/mL, 0.22 μm filtration, overnight hold at 2-8° C., and then final sampling, such that the flask treated with Benzonase® at infection had been exposed to Benzonase® for 8 days and those treated post harvest overnight.

Results

Figure 12:
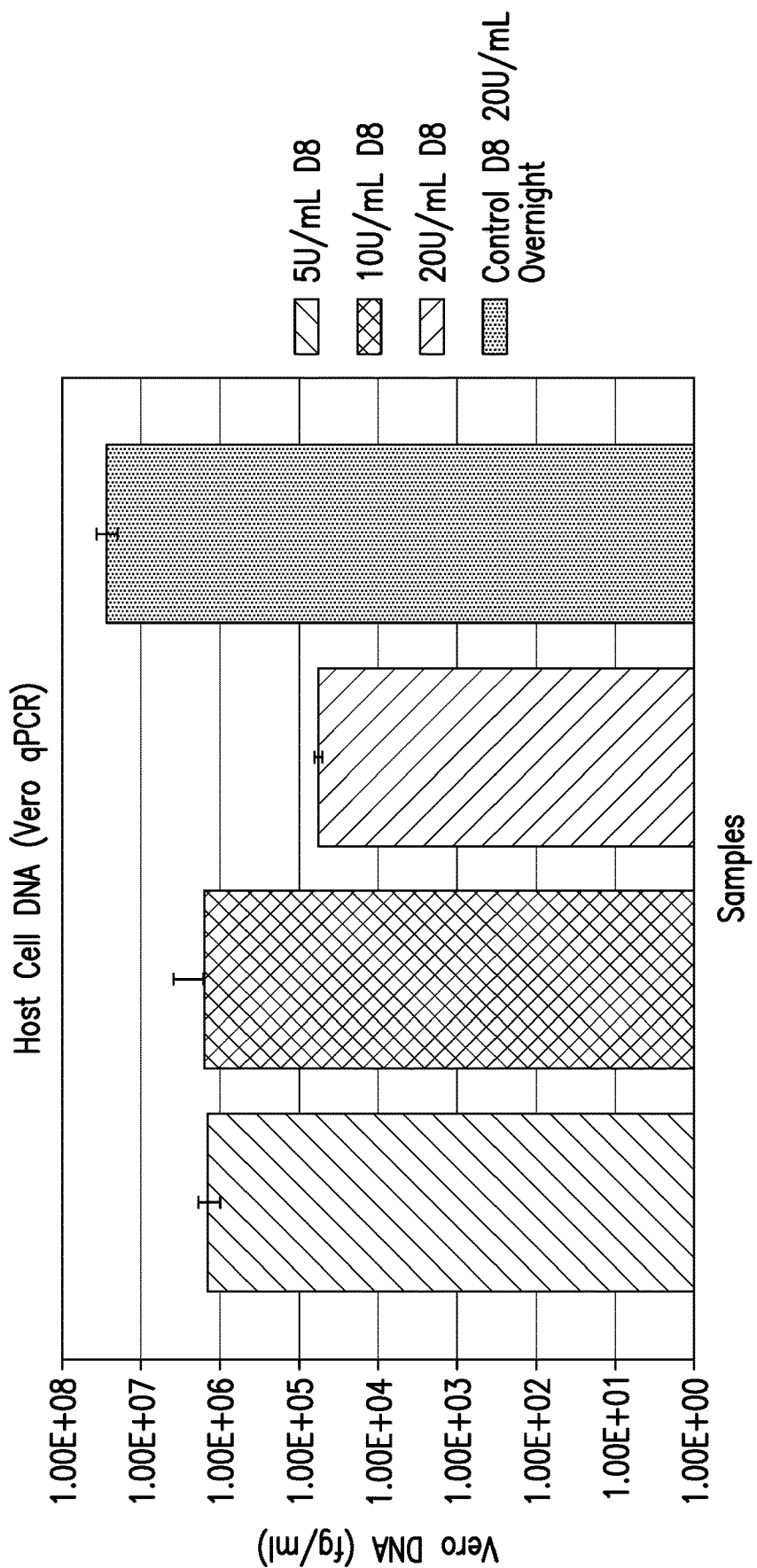
FIG. 12: Vero HcDNA in cell free supernatants as measured by qPCR on process samples from Dengue infected Vero harvests. Samples pulled after post harvest and post filtration overnight incubation. Error bars indicate standard deviation of three results, one from each flask, as each arm was run in triplicate.
Figure 13A:
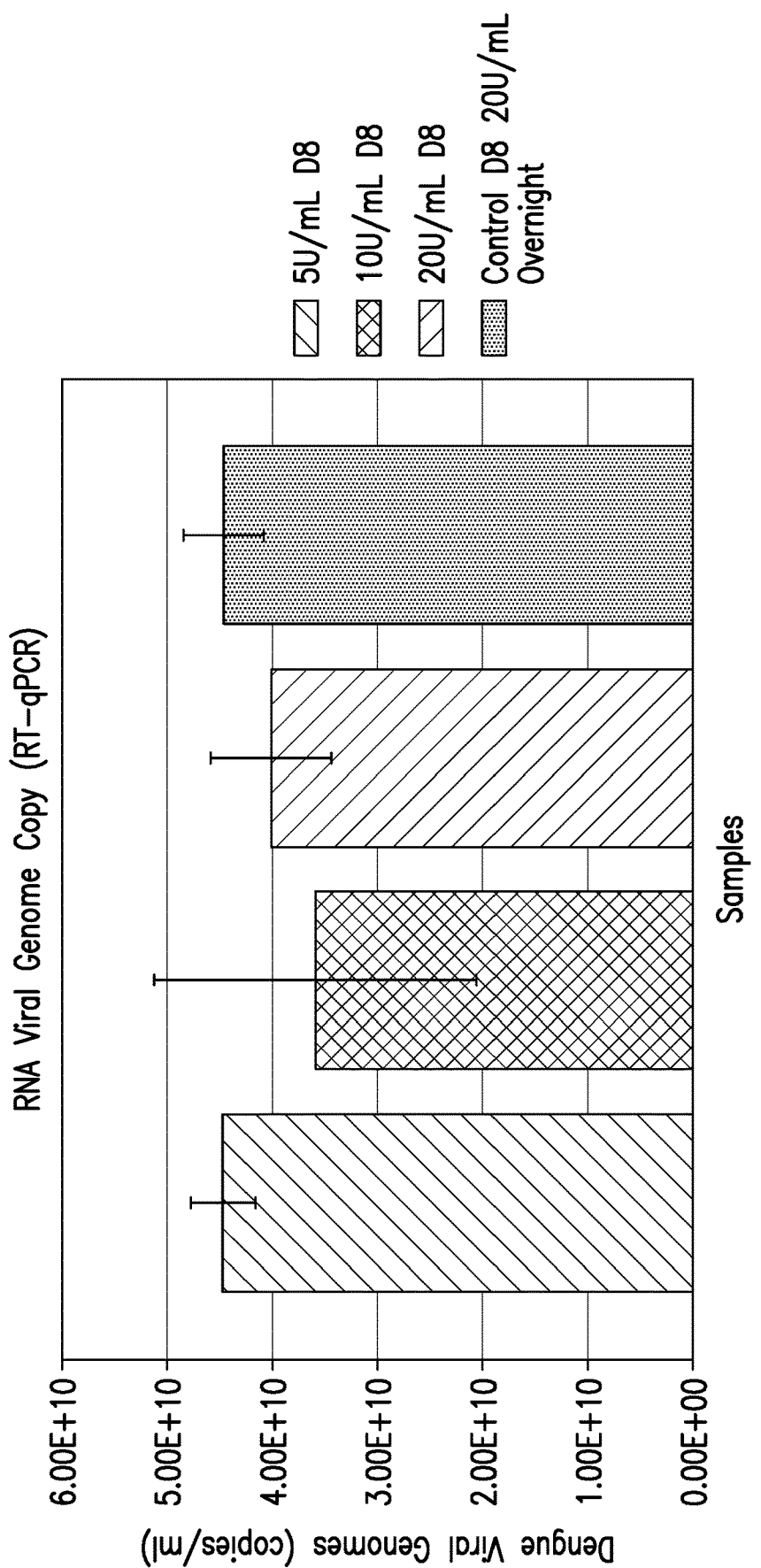
FIG. 13A-B: Dengue RNA genome qPCR and Dengue virus relative potency on samples pulled after overnight incubation (post harvest and post filtration). Error bars indicate standard deviation of three results, one from each flask, as each arm was run in triplicate.
Figure 13B:
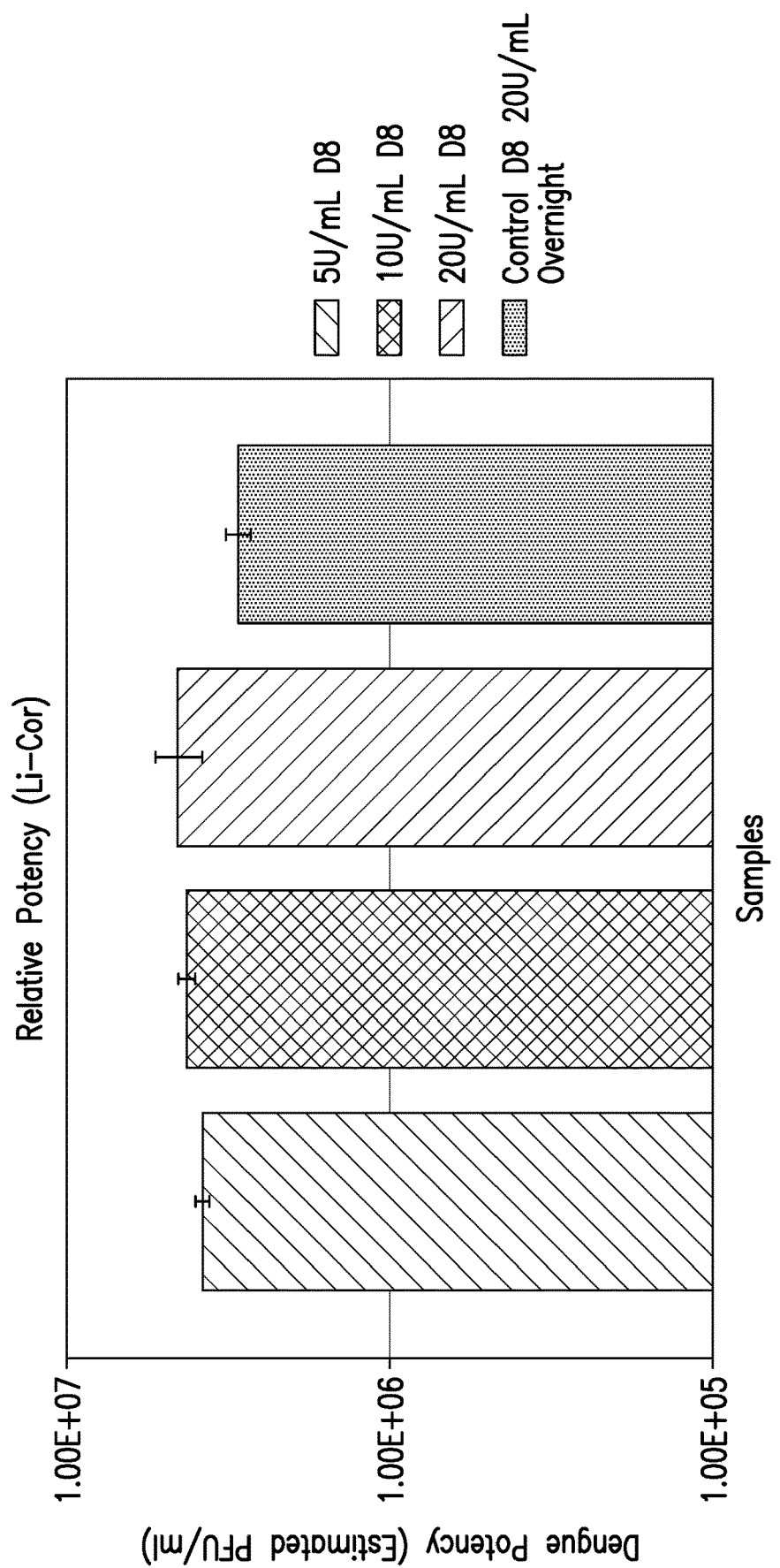

Analytical data on the final products from this experiment (after overnight hold) indicated:

1. Lower HcDNA content by qPCR in the experimental arms which included Benzonase® during infection than in the control arm. (See FIG. 12)
2. Virus production and infectivity was not negatively impacted by the presence of Benzonase® during infection, as the experimental arms had equivalent or greater viral RNA content (qPCR) and viral infectivity (Relative Potency) when compared to the control arm. (FIGS. 13A-B)

Conclusions

Given the presence of Benzonase® during infection of adherent cells, at less than or equal to the concentration used in the control arm (post harvest addition), resulted in less HcDNA and equivalent virus mass and infectivity, a benefit in HcDNA clearance was established when adding Benzonase® at infection as opposed to post-harvest. Specifically, a lower amount of HcDNA per vaccine dose can be achieved per amount of Benzonase® addition when performed at infection as opposed to when performing as a post-harvest unit operation, allowing for the realization of process cost savings through reduction in the amount of Benzonase® needed. In addition, a potential for logistical improvements exists, as removal of downstream Benzonase® incubations or other downstream unit operations meant to selectively remove HcDNA could be facilitated by the addition of Benzonase® during infection. In this case, the removal of an overnight incubation also presents a potential product quality benefit in that a lengthy hold step, during which unstable virus products could degrade, can be removed from the purification process.

Example 4: Benzonase® Digestion with Dengue Vaccine Candidate in 3 L Reactor Systems Containing Microcarriers Methods 1. Infection of 3 L Reactor Systems Vero cells are expanded and planted into two 3 L reactor systems containing microcarriers through a process similar to that described in Example 1. After appropriate cell growth in the 3 L reactors, the reactors are infected with Dengue serotype 4 virus. In this experiment, a comparison of Benzonase® addition during the culture or post-harvest is made.

2. Benzonase Digestion 2.1. Addition of Benzonase® to 3 L Reactors, Harvest and Purification In-culture Benzonase® treatment is tested against the post-harvest Benzonase® condition for the respective duplicate reactor. Accordingly, two reactors are treated with 20 U/mL Benzonase® one day prior to harvest. More specifically, a stock Benzonase® solution consisting of Benzonase® endonuclease is diluted in 50-100 mL culture media and added to two of the 3 L reactor systems to result in a final Benzonase® concentration of 20 units Benzonase® per mL cell culture. Following Benzonase® incubation the virus is harvested into a collection vessel and sampled for analysis. Post-harvest the virus is purified using the 1 day purification process detailed below 2.2. Post-harvest Benzonase Digestion Virus from the control reactor that had previously had no Benzonase® added is harvested and treated with 20 U/mL Benzonase® for overnight at 2-8° C. Specifically, Benzonase® endonuclease at 250,000 Units Benzonase® (U)/mL is added to the harvested virus to result in a final concentration of 20 untis Benzonase® per mL. Post addition the control arm is purified using the 2 day purification process detailed below.

2.3. Sampling of 3 L Reactor Systems

On harvest day virus is sampled and analyzed via on demand assays or aliquoted and frozen for later analytical characterization. On demand assays included measurements of cell count and viability via nucleo staining (Nucleocounter®) and supernatant metabolites via Bioprofile® (Nova Biomedical). Prior to freezing any sample, microcarriers are removed via a sieve.

3. Virus Purification 3.1. 1 Day Purification Process

Harvested virus that had been incubated with Benzonase® in the 3 L reactor are clarified by filtration using an Express SHC 0.5/0.2 um bilayer filter. Immediately following clarification the virus is concentrated (5× volume reduction) by means of tangential flow ultrafiltration across a 300 KDa nominal molecular weight cut-off flat-sheet membrane and diafiltered against 10 diavolumes of formulation buffer (11 mM Potassium Phosphate, 9% w/v sucrose, pH 7.5). Following diafiltration the virus is sterile filtered using an Express SHC 0.5/0.2 um bilayer filter. Throughout purification process intermediates are maintained at 2-8° C.

3.2. 2 Day Purification Process

Harvested virus from the control reactor is clarified by filtration using an Express SHC 0.5/0.2 um bilayer filter, immediately following Benzonase® addition. The filtered virus is incubated at 2-8° C. ovenight. The virus is then concentrated (5× volume reduction) by means of tangential flow ultrafiltration across a 300 KDa nominal molecular weight cut-off flat-sheet membrane and diafiltered against 10 diavolumes of formulation buffer (11 mM Potassium Phosphate, 9% w/v sucrose, pH 7.5). Following diafiltration the virus is sterile filtered using an Express SHC 0.5/0.2 um bilayer filter. Throughout purification process intermediates we maintained at 2-8° C.

3.3. Sampling of Key Process Intermediate

Samples of the following intermediates are taken throughout purification and frozen for later analytical characterization: Harvested virus (HV), filtered virus (FV), ultrafiltration concentrated retentate (UFCR), ultrafiltration final retentate (UFFR), and sterile filtered product (SFP).

What is claimed is:

1. A method for production of a flavivirus, comprising the steps of:
    a) infecting a culture of cells in a cell culture medium with the flavivirus; and
    b) incubating the cells in cell culture medium containing endonuclease for up to 15 days,
    wherein the endonuclease is added to the cell culture medium at any time from initial infection of the cells to prior to harvesting the cells and wherein the cells are adherent to a microcarrier.

2. The method of claim 1, wherein the endonuclease is added at the time of initial infection.

3. The method of claim 1, wherein the endonuclease is added from 0.5 to 15 days prior to harvesting the cells.

4. The method of claim 3, wherein the endonuclease is added 7, 8, 9, 10, 11, 12, 13, or 15 days prior to harvesting the cells.

5. The method of claim 1, wherein the endonuclease may have DNA specificity, RNA specificity, or both.

6. The method of claim 5, wherein the endonuclease is a broad spectrum endonuclease derived from the bacterium *Serratia marcescens*.

7. The method of claim 1, wherein the cell culture medium comprises endonuclease at an initial concentration of 2.5 to 80 U per mL of medium.

8. The method of claim 7, wherein the cell culture medium comprises endonuclease at an initial concentration of 2.5 to 20 U per mL.

9. The method of claim 8, wherein the cell culture medium comprises endonuclease at an initial concentration of 5 U per mL.

10. The method of claim 1, wherein the culture of cells are mammalian cells.

11. The method of claim 1, wherein the microcarrier is selected from microcarriers made of dextran, collagen, polystyrene, polyacrylamide, gelatin, glass, cellulose, polyethylene or plastic.

12. The method of claim 1, wherein the cell is a Vero cell.

13. The method of claim 1, wherein the flavivirus is a dengue virus, a live attenuated dengue virus, or a live attenuated chimeric flavivirus.

14. The method of claim 13, wherein the dengue virus, live attenuated dengue virus, or live attenuated chimeric flavivirus is a DEN1, DEN2, DEN3, or DEN4 virus.

15. The method of claim 13, wherein the flavivirus is a live attenuated chimeric flavivirus comprising the DEN2 prM and E genes on a DEN4 backbone.

16. The method of claim 15, wherein the flavivirus is rDEN2/4Δ30.

17. The method of claim 13, wherein the flavivirus is a live attenuated dengue virus selected from the group consisting of rDEN1Δ30, rDEN3Δ30/31, and rDEN4Δ30.

18. The method of claim 1, wherein trypsin is not added to the cell culture medium of step (b).

19. The method of claim 1, wherein the microcarrier is a dextran-based sphere with diethylaminoethyl functionality.

20. The method of claim 1 further comprising:
    a) harvesting infectious virus by collecting virus-containing supernatant obtained from centrifugation and/or filtration of the cell culture; and
    b) preparing a vaccine by subjecting the virus-containing supernatant to at least one processing step selected from the group consisting of chromatography, filtration, centrifugation, precipitation, concentrating, freezing, freeze-drying, and stabilizing by addition of a stabilizing agent.

* * * * *